United States Patent
Walton et al.

(10) Patent No.: US 7,194,042 B2
(45) Date of Patent: Mar. 20, 2007

(54) DATA TRANSMISSION WITH SPATIAL SPREADING IN A MIMO COMMUNICATION SYSTEM

(75) Inventors: Jay Rodney Walton, Carlisle, MA (US); John W. Ketchum, Harvard, MA (US); Mark S. Wallace, Bedford, MA (US); Steven J. Howard, Ashland, MA (US)

(73) Assignee: Qualcomm Incorporated, San Diego, CA (US)

( * ) Notice: Subject to any disclaimer, the term of this patent is extended or adjusted under 35 U.S.C. 154(b) by 0 days.

(21) Appl. No.: 11/009,200

(22) Filed: Dec. 9, 2004

(65) Prior Publication Data

US 2005/0157805 A1    Jul. 21, 2005

Related U.S. Application Data

(60) Provisional application No. 60/536,307, filed on Jan. 13, 2004.

(51) Int. Cl.
*H04B 7/02* (2006.01)
(52) U.S. Cl. .................. 375/267; 375/299; 375/130; 455/101
(58) Field of Classification Search ............... 375/267, 375/299, 347, 130, 146, 260, 295; 370/203, 370/204; 455/101
See application file for complete search history.

(56) References Cited

U.S. PATENT DOCUMENTS

| | | | |
|---|---|---|---|
| 6,804,307 B1* | 10/2004 | Popovic | 375/299 |
| 2002/0034217 A1 | 3/2002 | Zhang | |
| 2003/0112745 A1* | 6/2003 | Zhuang et al. | 370/208 |
| 2004/0081263 A1* | 4/2004 | Lee et al. | 375/347 |

FOREIGN PATENT DOCUMENTS

| | | |
|---|---|---|
| EP | 1009124 A2 * | 6/2000 |
| EP | 1223702 A1 * | 7/2002 |
| WO | WO 01/56218 | 8/2001 |

OTHER PUBLICATIONS

Yingxue Li, et al, "Transmit Diversity Over Quasi-Static Fading Channels Using Multiple Antennas and Random Signal Mapping," IEEE Trans. on Comm, vol. 51, No. 11, Nov. 2003.

(Continued)

*Primary Examiner*—Temesghen Ghebretinsae
(74) *Attorney, Agent, or Firm*—Thomas R. Rouse; Sandip (Mickey) S. Minhas; Dmitry R. Milikovsky

(57) ABSTRACT

For data transmission with spatial spreading, a transmitting entity (1) encodes and modulates each data packet to obtain a corresponding data symbol block, (2) multiplexes data symbol blocks onto $N_S$ data symbol streams for transmission on $N_S$ transmission channels of a MIMO channel, (3) spatially spreads the $N_S$ data symbol streams with steering matrices, and (4) spatially processes $N_S$ spread symbol streams for full-CSI transmission on $N_S$ eigenmodes or partial-CSI transmission on $N_S$ spatial channels of the MIMO channel. A receiving entity (1) obtains $N_R$ received symbol streams via $N_R$ receive antennas, (2) performs receiver spatial processing for full-CSI or partial-CSI transmission to obtain $N_S$ detected symbol streams, (3) spatially despreads the $N_S$ detected symbol streams with the same steering matrices used by the transmitting entity to obtain $N_S$ recovered symbol streams, and (4) demodulates and decodes each recovered symbol block to obtain a corresponding decoded data packet.

28 Claims, 8 Drawing Sheets

OTHER PUBLICATIONS

A. Goldsmith, et al, "Capacity Limits of MIMO Channels," IEEE JSAC, vol. 21, No. 5, Jun. 2003.

Huan Yao, "Efficient Signal, Code and Receiver Designs for MIMO Communications Systems," PhD Thesis, Massachusetts Institute of Technology, 2003.

T.L. Marzetta, B. Hassibi, B.M Hochwald, "Structured Unitary Space-Time Autocoding Constellations," IEEE Trans. on IT, vol. 48, No. 4, Apr. 2002.

W. Yu and J.M. Cioffi, "Trellis Precoding for the Broadcast Channel," Proc. Global Communications Conf., Oct. 2001, pp. 1344-1348.

F. R. Farrokhi, et al, "Link-Optimal Space-Time Processing with Multiple Transmit and Receive Antennas," IEEE Comm. Letters, vol. 5, No. 3, Mar. 2001.

B.M Hochwald, et al, "Systematic Design of Unitary Space-Time Constellations," IEEE Trans. on IT, vol. 46, No. 6, Sep. 2000.

B. M. Hochwald and T.L. Marzetta, "Unitary Space-Time Modulation for Multiple-Antenna Communications in Rayleigh Flat Fading," IEEE Trans. on IT, vol. 46, No. 2, Mar. 2000.

S. M. Alamouti, "A Simple Transmit Diversity Technique for Wireless Communications," IEEE JSAC, vol. 16, pp. 1451-1458, Oct. 1998.

Doostnejad et al., "Space-Time Spreading Codes for a Multiuser MIMO System," Institute of Electrical and Electronics Engineers, Conference Record of the 36th Asilomar Conference on Signals, Systems, & Computers, Pacific Grove, California, Nov. 3-6, vol. 1 of 2, Conference 36, pp. 1374-1378 (2002).

Medles et al., "Multistream space-time coding by spatial spreading, scrambling and delay diversity," IEEE International Conference on Acoustics, Speech, and Signal Processing Proceedings, Orlando, Florida, May 13-17, vol. 4 of 4, pp. 2429-2432 (2002).

Hanzo, Single and Multi-Carrier DS-CDMA, "Space-time spreading aided single-carrier wideband CDMA communicating over Multipath Nakagami Fading Channels," John Wiley & Sons, England, Chapter 8, pp. 279-310 (2003).

* cited by examiner

US 7,194,042 B2

DATA TRANSMISSION WITH SPATIAL SPREADING IN A MIMO COMMUNICATION SYSTEM

I. CLAIM OF PRIORITY UNDER 35 U.S.C. §119

The present Application for Patent claims priority to Provisional Application Ser. No. 60/536,307, entitled "Data Transmission with Spatial Spreading in a MIMO Communication System," filed Jan. 13, 2004, and assigned to the assignee hereof and hereby expressly incorporated by reference herein.

II. REFERENCE TO CO-PENDING APPLICATIONS FOR PATENT

The present Application for Patent is related to the following co-pending U.S. Patent Applications:

"Spatial Spreading in a Multi-Antenna Communication System" by Walton et al., having Ser. No. 11/008,865, filed concurrently herewith, assigned to the assignee hereof, and expressly incorporated by reference herein; and "Broadcast Transmission with Spatial Spreading in a Multi-Antenna Communication System" by Walton et al., having Ser. No. 11/009,824, filed concurrently herewith, assigned to the assignee hereof, and expressly incorporated by reference herein.

BACKGROUND

III. Field

The present invention relates generally to communication, and more specifically to techniques for transmitting data in a multiple-input multiple-output (MIMO) communication system.

IV. Background

A MIMO system employs multiple ($N_T$) transmit antennas at a transmitting entity and multiple ($N_R$) receive antennas at a receiving entity for data transmission. A MIMO channel formed by the $N_T$ transmit antennas and $N_R$ receive antennas may be decomposed into $N_S$ spatial channels, where $N_S \leq \min\{N_T, N_R\}$. The $N_S$ spatial channels may be used to transmit data in parallel to achieve higher throughput and/or redundantly to achieve greater reliability.

The MIMO channel between the transmitting entity and the receiving entity may experience various deleterious channel conditions such as, e.g., fading, multipath, and interference effects. In general, good performance may be achieved for data transmission via the MIMO channel if the interference and noise observed at the receiving entity are spatially "white", which is flat or constant interference and noise power across spatial dimension. This may not be the case, however, if the interference is from interfering sources located in specific directions. If the interference is spatially "colored" (not white), then the receiving entity can ascertain the spatial characteristics of the interference and place beam nulls in the direction of the interfering sources. The receiving entity may also provide the transmitting entity with channel state information (CSI). The transmitting entity can then spatially process data in a manner to maximize signal-to-noise-and-interference ratio (SNR) at the receiving entity. Good performance can thus be achieved when the transmitting and receiving entities perform the appropriate transmit and receive spatial processing for the data transmission in the presence of spatially colored interference.

To perform spatial nulling of interference, the receiving entity typically needs to ascertain the characteristics of the interference. If the interference characteristics change over time, then the receiving entity would need to continually obtain up-to-date interference information in order to accurately place the beam nulls. The receiving entity may also need to continually send channel state information at a sufficient rate to allow the transmitting entity to perform the appropriate spatial processing. The need for accurate interference information and channel state information renders spatial nulling of interference not practical for most MIMO systems.

There is therefore a need in the art for techniques to transmit data in the presence of spatially colored interference and noise.

DETAILED DESCRIPTION

The word "exemplary" is used herein to mean "serving as an example, instance, or illustration." Any embodiment described herein as "exemplary" is not necessarily to be construed as preferred or advantageous over other embodiments.

Techniques for transmitting data with spatial spreading in single-carrier and multi-carrier MIMO systems are described herein. Spatial spreading refers to the transmission of a data symbol (which is a modulation symbol for data) on multiple eigenmodes or spatial channels (described below) of a MIMO channel simultaneously with a steering vector. The spatial spreading randomizes a transmission channel observed by a stream of data symbols, which effectively whitens the transmitted data symbol stream and can provide various benefits as described below.

For data transmission with spatial spreading, a transmitting entity processes (e.g., encodes, interleaves, and modulates) each data packet to obtain a corresponding block of data symbols and multiplexes data symbol blocks onto $N_S$ data symbol streams for transmission on $N_S$ transmission channels in a MIMO channel. The transmitting entity then spatially spreads the $N_S$ data symbol streams with steering matrices to obtain $N_S$ spread symbol streams. The transmitting entity further spatially processes the $N_S$ spread symbol streams for either full-CSI transmission on $N_S$ eigenmodes of the MIMO channel or partial-CSI transmission on $N_S$ spatial channels of the MIMO channel, as described below.

A receiving entity obtains $N_R$ received symbol streams via $N_R$ receive antennas and performs receiver spatial processing for full-CSI or partial-CSI transmission to obtain $N_S$ detected symbol streams, which are estimates of the $N_S$ spread symbol streams. The receiving entity further spatially despreads the $N_S$ detected symbol streams with the same steering matrices used by the transmitting entity and obtains $N_S$ recovered symbol streams, which are estimates of the $N_S$ data symbol streams. The receiver spatial processing and spatial despreading may be performed jointly or separately. The receiving entity then processes (e.g., demodulates, deinterleaves, and decodes) each block of recovered symbols in the $N_S$ recovered symbol streams to obtain a corresponding decoded data packet.

The receiving entity may also estimate the signal-to-noise-and-interference ratio (SNR) of each transmission channel used for data transmission and select a suitable rate for the transmission channel based on its SNR. The same or different rates may be selected for the $N_S$ transmission channels. The transmitting entity encodes and modulates data for each transmission channel based on its selected rate.

Various aspects and embodiments of the invention are described in further detail below.

Figure 1:
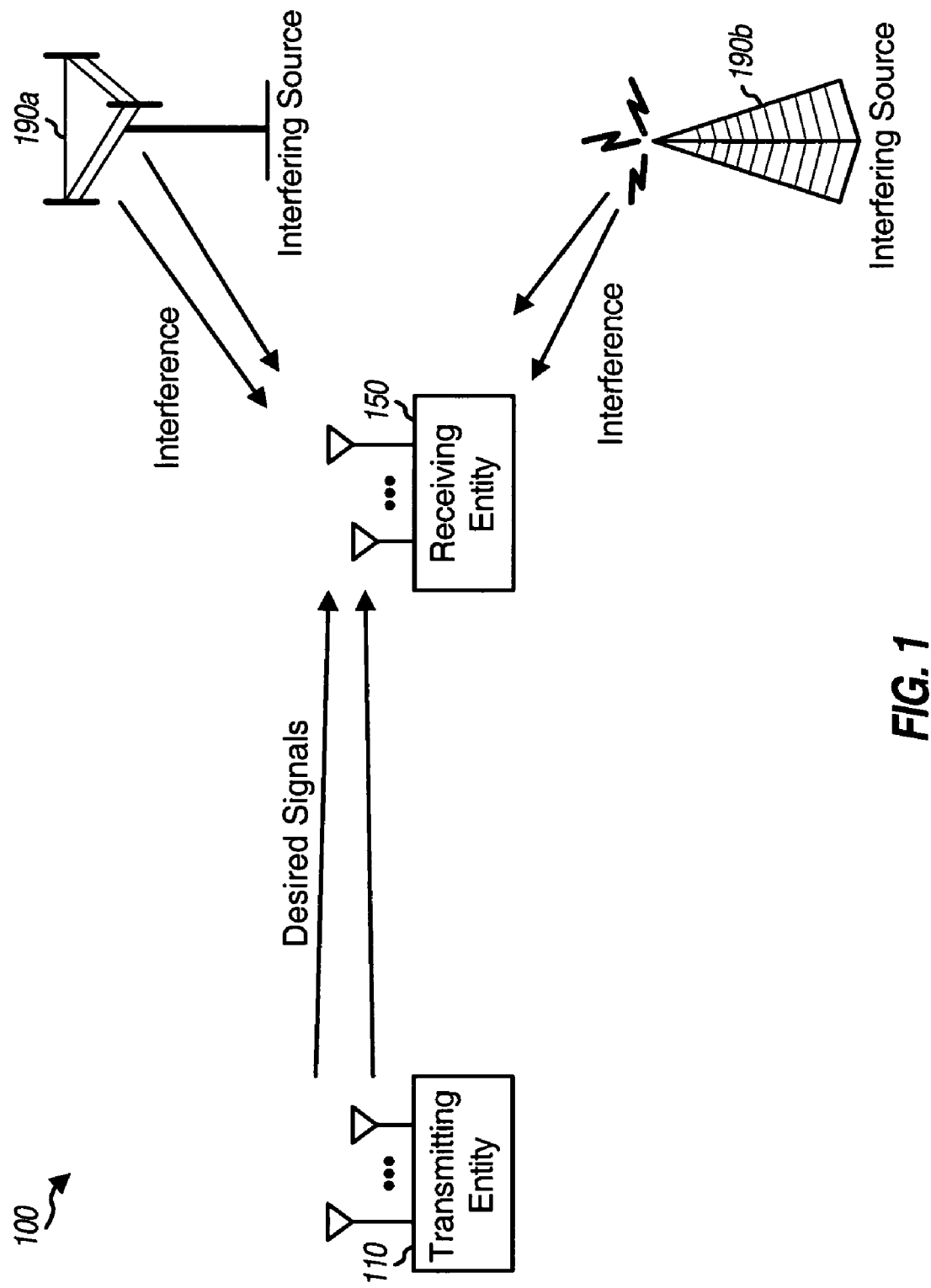
FIG. 1 shows a MIMO system with a transmitting entity, a receiving entity, and two interfering sources.

FIG. 1 shows a MIMO system 100 with a transmitting entity 110, a receiving entity 150, and two interfering sources 190a and 190b. Transmitting entity 110 transmits data to receiving entity 150 via line-of-sight paths (as shown in FIG. 1) and/or reflected paths (not shown in FIG. 1). Interfering sources 190a and 190b transmit signals that act as interference at receiving entity 150. The interference observed by receiving entity 150 from interfering sources 190a and 190b may be spatially colored.

1. Single-Carrier MIMO System

For a single-carrier MIMO system, a MIMO channel formed by the $N_T$ transmit antennas at the transmitting entity and the $N_R$ receive antennas at the receiving entity may be characterized by an $N_R \times N_T$ channel response matrix H, which may be expressed as:

$$\underline{H} = \begin{bmatrix} h_{1,1} & h_{1,2} & \cdots & h_{1,N_T} \\ h_{2,1} & h_{2,2} & \cdots & h_{2,N_T} \\ \vdots & \vdots & \ddots & \vdots \\ h_{N_R,1} & h_{N_R,2} & \cdots & h_{N_R,N_T} \end{bmatrix}, \quad \text{Eq (1)}$$

where entry $h_{i,j}$, for $i=1 \ldots N_R$ and $j=1 \ldots N_T$, denotes the coupling or complex channel gain between transmit antenna j and receive antenna i.

Data may be transmitted in various manners in the MIMO system. For a full-CSI transmission scheme, data is transmitted on "eigenmodes" of the MIMO channel (described below). For a partial-CSI transmission scheme, data is transmitted on spatial channels of the MIMO channel (also described below).

A. Full-CSI Transmission

For the full-CSI transmission scheme, eigenvalue decomposition may be performed on a correlation matrix of H to obtain $N_S$ eigenmodes of H, as follows:

$$R = H^H \cdot H = E \cdot \Lambda \cdot E^H, \quad \text{Eq (2)}$$

where R is an $N_T \times N_T$ correlation matrix of H;

E is an $N_T \times N_T$ unitary matrix whose columns are eigenvectors of R;

$\Lambda$ is an $N_T \times N_T$ diagonal matrix of eigenvalues of R; and

"$H$" denotes a conjugate transpose.

A unitary matrix U is characterized by the property $U^H \cdot U = I$, where I is the identity matrix. The columns of a unitary matrix are orthogonal to one another.

The transmitting entity may perform spatial processing with the eigenvectors of R to transmit data on the $N_S$ eigenmodes of H. The eigenmodes may be viewed as orthogonal spatial channels obtained through decomposition. The diagonal entries of $\Lambda$ are eigenvalues of R which represent the power gains for the $N_S$ eigenmodes.

The transmitting entity performs spatial processing for full-CSI transmission as follows:

$$x = E \cdot s, \quad \text{Eq (3)}$$

where s is an $N_T \times 1$ vector with $N_S$ non-zero entries for $N_S$ data symbols to be transmitted simultaneously on the $N_S$ spatial channels; and x is an $N_T \times 1$ vector with $N_T$ transmit symbols to be sent from the $N_T$ transmit antennas.

The received symbols at the receiving entity may be expressed as:

$$r = H \cdot x + j, \quad \text{Eq (4)}$$

where r is an $N_R \times 1$ vector with $N_R$ received symbols obtained via the $N_R$ receive antennas; and j is an $N_R \times 1$ vector of interference and noise observed at the receiving entity.

The receiving entity performs spatial processing with an $N_T \times N_R$ spatial filter matrix $M = \Lambda^{-1} \cdot E^H \cdot H^H$ for full-CSI transmission, as follows:

$$\begin{aligned} \hat{s} &= M \cdot r \\ &= \Lambda^{-1} \cdot E^H \cdot H^H \cdot (H \cdot E \cdot s + \underline{j}) \\ &= \underline{\Lambda^{-1} \cdot E^H \cdot E \cdot \Lambda \cdot E^H \cdot E \cdot s} + \Lambda^{-1} \cdot E^H \cdot H^H \cdot \underline{j} \\ &= s + \underline{\tilde{j}} \end{aligned} \quad \text{Eq (5)}$$

where $\hat{s}$ is an $N_T \times 1$ vector with $N_S$ recovered symbols or data symbol estimates, which are estimates of the $N_S$ data symbols in s; and $\tilde{j} = \Lambda^{-1} \cdot E^H \cdot H^H \cdot j$ is the "post-detection" interference and noise after the spatial processing at the receiving entity.

An eigenmode may be viewed as an effective channel between an element of s and a corresponding element of $\hat{s}$ with the transmitting and receiving entities performing the spatial processing shown in equations (3) and (5), respectively. The transmitting and receiving entities typically only have estimates of the channel response matrix H, which may be obtained based on pilot symbols. A pilot symbol is a modulation symbol for pilot, which is data that is known a priori by both the transmitting and receiving entities. For simplicity, the description herein assumes no channel estimation error.

The vector j may be decomposed into an interference vector i and a noise vector n, as follows:

$$j = i + n. \quad \text{Eq (6)}$$

The noise may be characterized by an $N_R \times N_R$ autocovariance matrix $\phi_{nn} = E[n \cdot n^H]$, where E[x] is the expected value of x. If the noise is additive white Gaussian noise (AWGN) with zero mean and a variance of $\sigma_n^2$, then the noise autocovariance matrix may be expressed as: $\phi_{nn} = \sigma_n^2 \cdot I$. Similarly, the interference may be characterized by an $N_R \times N_R$ autocovariance matrix $\phi_{ii}=E[i \cdot i^H]$. The autocovariance matrix of j may be expressed as $\phi_{jj}=E[j \cdot j^H]=\phi_{nn}+\phi_{ii}$, assuming the interference and noise are uncorrelated.

The interference and noise are considered to be spatially white if their autocovariance matrices are of the form $\sigma^2 \cdot I$ due to the noise and interference being uncorrelated. For spatially white interference and noise, each receive antenna observes the same amount of interference and noise, and the interference and noise observed at each receive antenna are uncorrelated with the interference and noise observed at all other receive antennas. For spatially colored interference and noise, the autocovariance matrices have non-zero off-diagonal terms due to correlation between the interference and noise observed at different receive antennas. In this case, each receive antenna i may observe a different amount of interference and noise, which is equal to the sum of the $N_R$ elements in the i-th row of the matrix $\phi_{jj}$.

If the interference and noise are spatially colored, then the optimal eigenvectors for full-CSI transmission may be derived as:

$$R_{opt}=H^H \phi_{jj}^{-1} \cdot H = E_{opt} \cdot \Lambda \cdot E_{opt}^H. \qquad \text{Eq (7)}$$

The eigenvectors $E_{opt}$ steer the data transmission in the direction of the receiving entity and further place beam nulls in the direction of the interference. However, the transmitting entity would need to be provided with the autocovariance matrix $\phi_{jj}$ in order to derive the eigenvectors $E_{opt}$. The matrix $\phi_{jj}$ is based on the interference and noise observed at the receiving entity and can only be determined by the receiving entity. To spatially null the interference, the receiving entity would need to send this matrix, or its equivalent, back to the transmitting entity, which can represent a large amount of channel state information to send back.

Spatial spreading may be used to spatially whiten the interference and noise observed by the receiving entity and may potentially improve performance. The transmitting entity performs spatial spreading with an ensemble of steering matrices such that the complementary spatial despreading at the receiving entity spatially whitens the interference and noise.

For full-CSI transmission with spatial spreading, the transmitting entity performs processing as follows:

$$x_{fcsi}(m)=E(m) \cdot V(m) \cdot s(m), \qquad \text{Eq (8)}$$

where s(m) is a data symbol vector for transmission span m;

V(m) is an $N_T \times N_T$ steering matrix for transmission span m;

E(m) is a matrix of eigenvectors for transmission span m; and $x_{fcsi}(m)$ is a transmit symbol vector for transmission span m.

A transmission span may cover time and/or frequency dimensions. For example, in a single-carrier MIMO system, a transmission span may correspond to one symbol period, which is the time duration to transmit one data symbol. A transmission span may also cover multiple symbol periods. As shown in equation (8), each data symbol in s(m) is spatially spread with a respective column of V(m) to obtain $N_T$ spread symbols, which may then be transmitted on all eigenmodes of H(m).

The received symbols at the receiving entity may be expressed as:

$$r_{fcsi}(m)=H(m) \cdot x_{fcsi}(m)+j(m)=H(m) \cdot E(m) \cdot V(m) \cdot s(m)+j(m). \qquad \text{Eq (9)}$$

The receiving entity derives a spatial filter matrix $M_{fcsi}(m)$ as follows:

$$M_{fcsi}(m)=\Lambda^{-1}(m) \cdot E^H(m) \cdot H^H(m). \qquad \text{Eq (10)}$$

The receiving entity performs receiver spatial processing and spatial despreading using $M_{fcsi}(m)$ and $V^H(m)$, respectively, as follows:

$$\begin{aligned}
\hat{s}_{fcsi}(m) &= \underline{V}^H(m) \cdot \underline{M}_{fcsi}(m) \cdot \underline{r}_{fcsi}(m), \qquad \text{Eq (11)} \\
&= \underline{V}^H(m) \cdot \Lambda^{-1}(m) \cdot \underline{E}^H(m) \cdot \underline{H}^H(m) \cdot \\
&\quad [\underline{H}(m) \cdot \underline{E}(m) \cdot \underline{V}(m) \cdot \underline{s}(m) + \underline{j}(m)], \\
&= \underline{s}(m) + \underline{j}_{fcsi}(m),
\end{aligned}$$

where $j_{fcsi}(m)$ is the "post-detection" interference and noise after the spatial processing and spatial despreading at the receiving entity, which is:

$$j_{fcsi}(m)=V^H(m) \cdot \Lambda^{-1}(m) \cdot E^H(m) \cdot H^H(m) \cdot j(m). \qquad \text{Eq (12)}$$

As shown in equation (12), the received interference and noise in j(m) are transformed by the conjugate transposes of V(m), E(m), and H(m). E(m) is a matrix of eigenvectors that may not be optimally computed for spatially colored interference and noise if the autocovariance matrix $\phi_{jj}(m)$ is not known, which is often the case. The transmitting and receiving entities may, by random chance, operate with a matrix E(m) that results in more interference and noise being observed by the receiving entity. This may be the case, for example, if a mode of E(m) is correlated with the interference. If the MIMO channel is static, then the transmitting and receiving entities may continually operate with a matrix E(m) that provides poor performance. The spatial despreading with the steering matrix V(m) spatially whitens the interference and noise. The effectiveness of the interference and noise whitening is dependent on the characteristics of the channel response matrix H(m) and the interference j(m). If a high degree of correlation exists between the desired signal and the interference, then this limits the amount of gain provided by the whitening of the interference and noise.

The SNR of each eigenmode with full-CSI transmission may be expressed as:

$$\gamma_{fcsi,\ell}(k) = \frac{P_\ell(m)\lambda_\ell(m)}{\sigma_j^2}, \quad \text{for } \ell = 1 \ldots N_S, \qquad \text{Eq (13)}$$

where $P_l(m)$ is the transmit power used for the transmit symbol sent on eigenmode l in transmission span m;

$\lambda_l(m)$ is the eigenvalue for eigenmode l in transmission span m, which is the l-th diagonal element of $\Lambda(m)$;

$\sigma_j^2$ is the variance of the received interference and noise; and $\gamma_{fcsi,l}(m)$ is the SNR of eigenmode l in transmission span m.

B. Partial-CSI Transmission

For partial-CSI transmission with spatial spreading, the transmitting entity performs processing as follows:

$$x_{pcsi}(m)=V(m) \cdot s(m), \qquad \text{Eq (14)}$$

where $x_{pcsi}(m)$ is the transmit data vector for transmission span m. As shown in equation (14), each data symbol in s(m) is spatially spread with a respective column of V(m) to obtain $N_T$ spread symbols, which may then be transmitted from all $N_T$ transmit antennas.

The received symbols at the receiving entity may be expressed as:

$$r_{pcsi}(m)=H(m) \cdot V(m) \cdot s(m)+j(m)=H_{eff}(m) \cdot s(m)+j(m), \quad \text{Eq (15)}$$

where $r_{pcsi}(m)$ is the received symbol vector for transmission span m; and $H_{eff}(m)$ is an effective channel response matrix, which is:

$$H_{eff}(m)=H(m) \cdot V(m). \quad \text{Eq (16)}$$

The receiving entity may derive estimates of the transmitted data symbols in s using various receiver processing techniques. These techniques include a channel correlation matrix inversion (CCMI) technique (which is also commonly referred to as a zero-forcing technique), a minimum mean square error (MMSE) technique, a successive interference cancellation (SIC) technique, and so on. The receiving entity may perform receiver spatial processing and spatial despreading jointly or separately, as described below. In the following description, one data symbol stream is sent for each element of the data symbol vector s.

For the CCMI technique, the receiving entity may derive a spatial filter matrix $M_{ccmi}(m)$, as follows:

$$M_{ccmi}(m)=[H_{eff}^H(m) \cdot H_{eff}(m)]^{-1} \cdot H_{eff}^H(m)= R_{eff}^{-1}(m) \cdot H_{eff}^H(m). \quad \text{Eq (17)}$$

The receiving entity may then perform CCMI spatial processing and despreading jointly, as follows:

$$\hat{s}_{ccmi}(m) = \underline{M}_{ccmi}(m) \cdot r_{pcsi}(m), \quad \text{Eq (18)}$$
$$= R_{eff}^{-1}(m) \cdot \underline{H}_{eff}^H(m) \cdot [\underline{H}_{eff}(m) \cdot s(m) + \underline{j}(m)],$$
$$= \underline{s}(m) + \underline{j}_{ccmi}(m),$$

where $j_{ccmi}(m)$ is the CCMI filtered and despread interference and noise, which is:

$$J_{ccmi}(m)=R_{eff}^{-1}(m) \cdot H_{eff}^H(m) \cdot j(m)=V^H(m) \cdot R^{-1}(m) \cdot H^H(m) \cdot j(m). \quad \text{Eq (19)}$$

As shown in equation (19), the interference and noise j(m) is whitened by $V^H(m)$. However, due to the structure of R(m), the CCMI technique may amplify the interference and noise.

The receiving entity may also perform CCMI spatial processing and spatial despreading separately, as follows:

$$\hat{s}_{ccmi}(m) = \underline{V}^H(m) \cdot \tilde{\underline{M}}_{ccmi}(m) \cdot r_{pcsi}(m), \quad \text{Eq (20)}$$
$$= \underline{V}^H(m) \cdot \underline{R}^{-1}(m) \cdot \underline{H}^H(m) \cdot$$
$$[\underline{H}(m) \cdot \underline{V}(m) \cdot s(m) + \underline{j}(m)],$$
$$= \underline{s}(m) + \underline{j}_{ccmi}(m),$$

where $\tilde{M}_{ccmi}(m)=R^{-1}(m) \cdot H^H(m)$. In any case, a spatial channel may be viewed as an effective channel between an element of s and a corresponding element of ŝ with the transmitting entity performing spatial processing with the identity matrix I and the receiving entity performing the appropriate receiver spatial processing to estimate s.

The SNR for the CCMI technique may be expressed as:

$$\gamma_{ccmi,\ell}(m) = \frac{P_\ell(m)}{r_{\ell\ell}(m) \sigma_j^2}, \quad \text{for } \ell = 1 \ldots N_S, \quad \text{Eq (21)}$$

where $P_l(m)$ is the power used for data symbol stream $\{s_l\}$ in transmission span m;

$r_{ll}(m)$ is the l-th diagonal element of $R_{eff}^{-1}(m)$;

$\sigma_j^2$ is the variance of the received interference and noise; and $\gamma_{ccmi,l}(m)$ is the SNR of data symbol stream $\{s_l\}$ in transmission span m.

The quantity $P_l(m)/\sigma_j^2$ is the SNR of data symbol stream $\{s_l\}$ at the receiving entity prior to the receiver spatial processing and is commonly referred to as the received SNR. The quantity $\gamma_{ccmi,l}(m)$ is the SNR of data symbol stream $\{s_l\}$ after the receiver spatial processing and is also referred to as the post-detection SNR. In the following description, "SNR" refers to post-detection SNR unless noted otherwise.

For the MMSE technique, the receiving entity may derive a spatial filter matrix $M_{mmse}(m)$, as follows:

$$M_{mmse}(m)=[H_{eff}^H(m) \cdot H_{eff}(m)+\phi_{jj}(m)]^{-1} \cdot H_{eff}^H(m). \quad \text{Eq (22)}$$

The spatial filter matrix $M_{mmse}(m)$ minimizes the mean square error between the symbol estimates from the spatial filter and the data symbols. If the autocovariance matrix $\phi_{jj}(m)$ is not known, which is often the case, then the spatial filter matrix $M_{mmse}(m)$ may be approximated as:

$$M_{mmse}(m)=[H_{eff}^H(m) \cdot H_{eff}(m)+\sigma_j^2 \cdot I]^{-1} \cdot H_{eff}^H(m). \quad \text{Eq (23)}$$

The receiving entity may perform MMSE spatial processing and despreading jointly, as follows:

$$\hat{s}_{mmse}(m) = D_Q(m) \cdot M_{mmse}(m) \cdot r_{pcsi}(m), \quad \text{Eq (24)}$$
$$= \underline{D}_Q(m) \cdot \underline{M}_{mmse}(m) \cdot [\underline{H}_{eff}(m) \cdot s(m) + \underline{j}(m)],$$
$$= \underline{D}_Q(m) \cdot \underline{Q}(m) \cdot \underline{s}(m) + \underline{j}_{mmse}(m),$$

where $Q(m)=M_{mmse}(m) \cdot H_{eff}(m)$;

$D_Q(m)$ is a diagonal matrix whose diagonal elements are the diagonal elements of $Q^{-1}(m)$, or $D_Q(m)=[\text{diag}[Q(m)]]^{-1}$; and $j_{mmse}(m)$ is the MMSE filtered and despread interference and noise, which is:

$$\underline{j}_{mmse}(m) = \underline{D}_Q(m) \cdot \underline{M}_{mmse}(m) \cdot \underline{j}(m), \quad \text{Eq (25)}$$
$$= \underline{D}_Q(m) \cdot [\underline{H}_{eff}^H(m) \cdot \underline{H}_{eff}(m) + \underline{\varphi}_{jj}(m)]^{-1} \cdot$$
$$\underline{H}_{eff}^H(m) \cdot \underline{j}(m).$$

The symbol estimates from the spatial filter matrix $M_{mmse}(m)$ are unnormalized estimates of the data symbols. The multiplication with $D_Q(m)$ provides normalized estimates of the data symbols. The receiving entity may also perform MMSE spatial processing and spatial despreading separately, similar to that described above for the CCMI technique.

The SNR for the MMSE technique may be expressed as:

$$\gamma_{mmse,\ell}(m) = \frac{q_{\ell\ell}(m)}{1 - q_{\ell\ell}(m)} P_\ell(m), \quad \text{for } \ell = 1 \ldots N_S, \qquad \text{Eq (26)}$$

where $q_{\ell\ell}(m)$ is the l-th diagonal element of $Q(m)$; and
$\gamma_{mmse,\ell}(m)$ is the SNR of data symbol stream $\{s_\ell\}$ in transmission span m.

For the SIC technique, the receiving entity processes the $N_R$ received symbol streams in $N_S$ successive stages to recover the $N_S$ data symbol streams. For each stage l, the receiving entity performs spatial processing and despreading on either the $N_R$ received symbol streams or $N_R$ modified symbol streams from the preceding stage (e.g., using the CCMI, MMSE, or some other technique) to obtain one recovered symbol stream $\{\hat{s}_\ell\}$. The receiving entity then processes (e.g., demodulates, deinterleaves, and decodes) this recovered symbol stream to obtain a corresponding decoded data stream $\{\hat{d}_\ell\}$. The receiving entity next estimates the interference this stream causes to the other data symbol streams not yet recovered. To estimate the interference, the receiving entity re-encodes, interleaves, and symbol maps the decoded data stream in the same manner performed at the transmitting entity for this stream and obtains a stream of "remodulated" symbols $\{\check{s}_\ell\}$, which is an estimate of the data symbol stream just recovered. The receiving entity then spatially spreads the remodulated symbol stream with the steering matrix V(m) and further multiplies the result with the channel response matrix H(m) for each transmission span of interest to obtain $N_R$ interference components caused by this stream. The $N_R$ interference components are then subtracted from the $N_R$ modified or received symbol streams for the current stage to obtain $N_R$ modified symbol streams for the next stage. The receiving entity then repeats the same processing on the $N_R$ modified symbol streams to recover another data stream.

For the SIC technique, the SNR of each data symbol stream is dependent on (1) the spatial processing technique (e.g., CCMI or MMSE) used for each stage, (2) the specific stage in which the data symbol stream is recovered, and (3) the amount of interference due to the data symbol streams not yet recovered. In general, the SNR progressively improves for data symbol streams recovered in later stages because the interference from data symbol streams recovered in prior stages is canceled. This then allows higher rates to be used for data symbol streams recovered in later stages.

C. System Model

Figure 2:
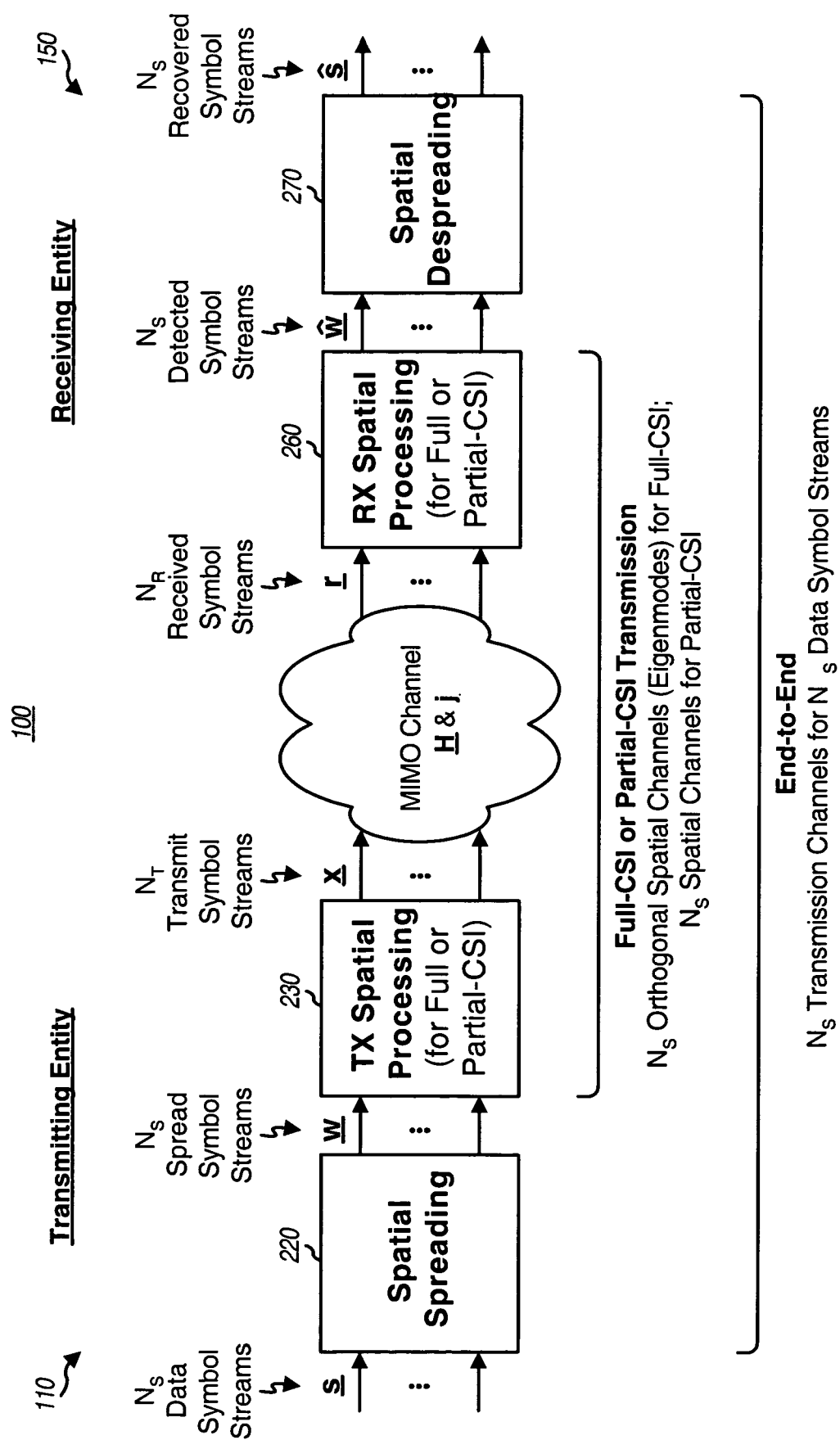
FIG. 2 shows a model for data transmission with spatial spreading.

FIG. 2 shows a model for data transmission with spatial spreading. Transmitting entity 110 performs spatial spreading (block 220) and spatial processing for full-CSI or partial-CSI transmission (block 230). Receiving entity 150 performs receiver spatial processing for full-CSI or partial-CSI transmission (block 260) and spatial despreading (block 270). The description below makes references to the vectors shown in FIG. 2.

Figure 3:
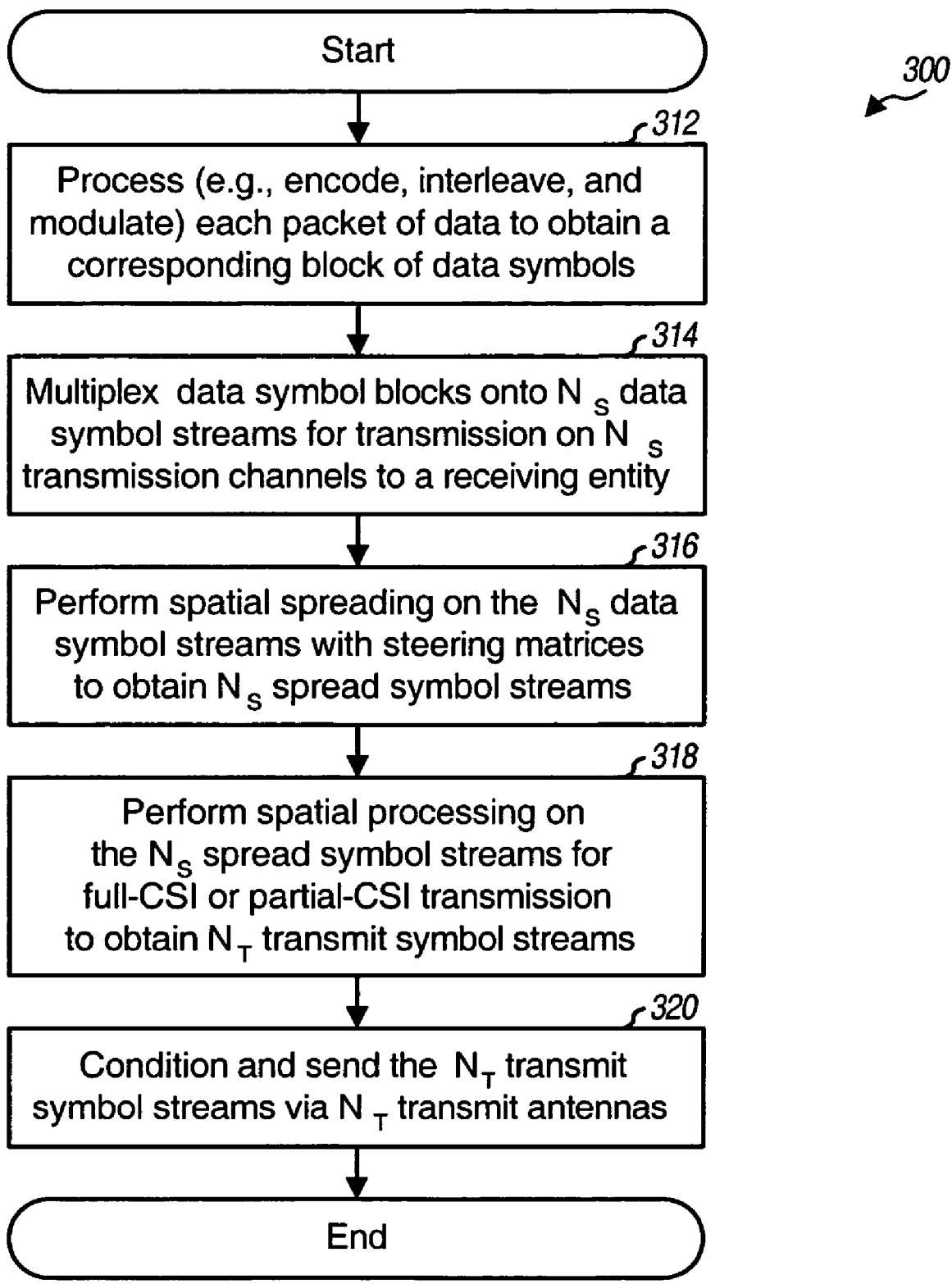
FIG. 3 shows the processing performed by the transmitting entity.

FIG. 3 shows a process 300 performed by the transmitting entity to transmit data with spatial spreading in the MIMO system. The transmitting entity processes (e.g., encodes and interleaves) each packet of data to obtain a corresponding block of coded data, which is also called a code block or a coded data packet (block 312). Each code block is encoded separately at the transmitting entity and decoded separately at the receiving entity. The transmitting entity further symbol maps each code block to obtain a corresponding block of data symbols (also block 312). The transmitting entity multiplexes all data symbol blocks generated for all data packets onto $N_S$ data symbol streams (denoted by vector s) (block 314). Each data symbol stream is sent on a respective transmission channel. The transmitting entity spatially spreads the $N_S$ data symbol streams with steering matrices and obtains $N_S$ spread symbol streams (denoted by a vector w in FIG. 2) (block 316). The spatial spreading is such that each data symbol block is spatially spread with multiple ($N_M$) steering matrices to randomize the transmission channel observed by the block. The randomization of the transmission channel results from using different steering matrices and not necessarily from randomness in the elements of the steering matrices. The transmitting entity further performs spatial processing on the $N_S$ spread symbol streams for full-CSI or partial-CSI transmission, as described above, and obtains $N_T$ transmit symbol streams (denoted by vector x) (block 318). The transmitting entity then conditions and sends the $N_T$ transmit symbol streams via the $N_T$ transmit antennas to the receiving entity (block 320).

Figure 4:
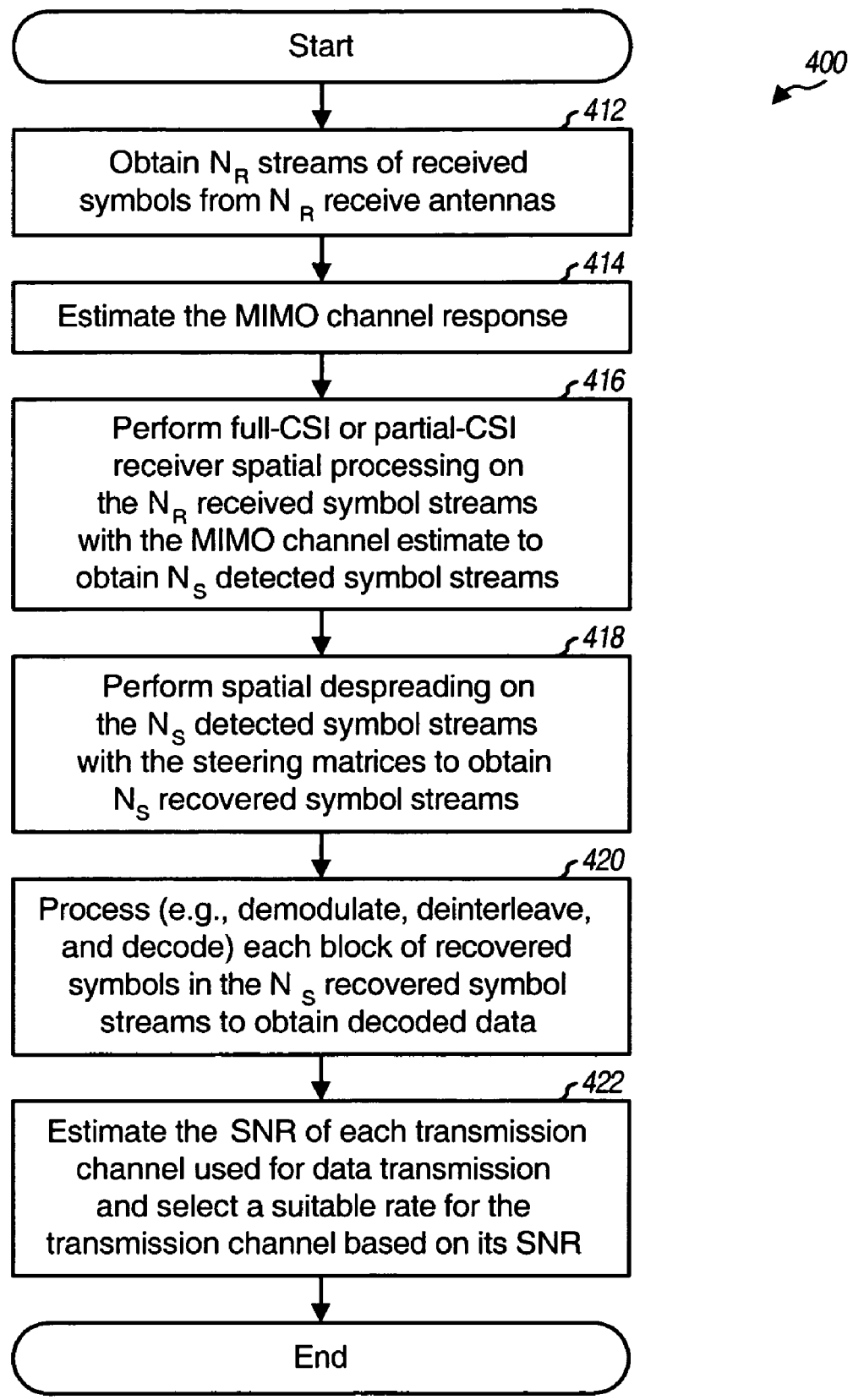
FIG. 4 shows the processing performed by the receiving entity.

FIG. 4 shows a process 400 performed by the receiving entity to receive data transmitted with spatial spreading in the MIMO system. The receiving entity obtains $N_R$ received symbol streams (denoted by vector r) via the $N_R$ receive antennas (block 412). The receiving entity estimates the response of the MIMO channel (block 414), performs spatial processing for full-CSI or partial-CSI transmission based on the MIMO channel estimate, and obtains $N_S$ detected symbol streams (denoted by a vector $\hat{w}$ in FIG. 2) (block 416). The receiving entity further spatially despreads the $N_S$ detected symbol streams with the same steering matrices used by the transmitting entity and obtains $N_S$ recovered symbol streams (denoted by vector $\hat{s}$) (block 418). The receiver spatial processing and spatial despreading may be performed jointly or separately, as described above. The receiving entity then processes (e.g., demodulates deinterleaves, and decodes) each block of recovered symbols in the $N_S$ recovered symbol streams to obtain a corresponding decoded data packet (block 420). The receiving entity may also estimate the SNR of each transmission channel used for data transmission and select a suitable rate for the transmission channel based on its SNR (block 422). The same or different rates may be selected for the $N_S$ transmission channels.

Referring back to FIG. 2, the $N_S$ data symbol streams are sent on $N_S$ transmission channels of the MIMO channel. Each transmission channel is an effective channel observed by a data symbol stream between an element of the vector s at the transmitting entity and a corresponding element of the vector $\hat{s}$ at the receiving entity (e.g., the l-th transmission channel is the effective channel between the l-th element of s and the l-th element of $\hat{s}$). The spatial spreading randomizes the $N_S$ transmission channels. The $N_S$ spread symbol streams are sent on either the $N_S$ eigenmodes of the MIMO channel for full-CSI transmission or the $N_S$ spatial channels of the MIMO channel for partial-CSI transmission.

D. Spatial Spreading

The steering matrices used for spatial spreading may be generated in various manners, as described below. In one embodiment, a set of L steering matrices is generated and denoted as $\{V\}$, or V(i) for i=1 . . . L, where L may be any integer greater than one. These steering matrices are unitary matrices having orthogonal columns. Steering matrices from this set are selected and used for spatial spreading.

The spatial spreading may be performed in various manners. In general, it is desirable to use as many different steering matrices as possible for each data symbol block so that the interference and noise are randomized across the block. Each data symbol block is transmitted in $N_M$ transmission spans, where $N_M>1$, and $N_M$ is also referred to as the block length. One steering matrix in the set may be used for each transmission span. The transmitting and receiving entities may be synchronized such that both entities know which steering matrix to use for each transmission span. With spatial spreading, the receiving entity observes a distribution of interference and noise across each data symbol block even if the MIMO channel is constant across the entire block. This avoids the case in which high levels of interference and noise are received because the transmitting and receiving entities continually use a bad matrix of eigenvectors or the receiving entity continually observes colored interference.

The L steering matrices in the set may be selected for use in various manners. In one embodiment, the steering matrices are selected from the set in a deterministic manner. For example, the L steering matrices may be cycled through and selected in sequential order, starting with the first steering matrix V(1), then the second steering matrix V(2), and so on, and then the last steering matrix V(L). In another embodiment, the steering matrices are selected from the set in a pseudo-random manner. For example, the steering matrix to use for each transmission span m may be selected based on a function f(m) that pseudo-randomly selects one of the L steering matrices, or steering matrix V(f(m)). In yet another embodiment, the steering matrices are selected from the set in a "permutated" manner. For example, the L steering matrices may be cycled through and selected for use in sequential order. However, the starting steering matrix for each cycle may be selected in a pseudo-random manner, instead of always being the first steering matrix V(1). The L steering matrices may also be selected in other manners, and this is within the scope of the invention.

The steering matrix selection may also be dependent on the number of steering matrices (L) in the set and the block length ($N_M$). In general, the number of steering matrices may be greater than, equal to, or less than the block length. Steering matrix selection for these three cases may be performed as described below.

If $L=N_M$, then the number of steering matrices matches the block length. In this case, a different steering matrix may be selected for each of the $N_M$ transmission spans used to send each data symbol block. The $N_M$ steering matrices for the $N_M$ transmission spans may be selected in a deterministic, pseudo-random, or permutated manner, as described above.

If $L<N_M$, then the block length is longer than the number of steering matrices in the set. In this case, the steering matrices are reused for each data symbol block and may be selected as described above.

If $L>N_M$, then a subset of the steering matrices is used for each data symbol block. The selection of the specific subset to use for each data symbol block may be deterministic or pseudo-random. For example, the first steering matrix to use for the current data symbol block may be the steering matrix after the last one used for a prior data symbol block.

As noted above, a transmission span may cover one or multiple symbol periods and/or one or multiple subbands. For improved performance, it is desirable to select the transmission span to be as small as possible so that (1) more steering matrices can be used for each data symbol block and (2) each receiving entity can obtain as many "looks" of the MIMO channel as possible for each data symbol block. The transmission span should also be shorter than the coherence time of the MIMO channel, which is the time duration over which the MIMO channel can be assumed to be approximately static. Similarly, the transmission span should be smaller than the coherence bandwidth of the MIMO channel for a wideband system (e.g., an OFDM system).

E. Applications for Spatial Spreading

Spatial spreading may be used to randomize and whiten spatially colored interference and noise for both full-CSI and partial-CSI transmission, as described above. This may improve performance for certain channel conditions.

Spatial spreading may also be used to reduce outage probability under certain operating scenarios. As an example, a block of data symbols for a code block may be partitioned into $N_T$ data symbol subblocks. Each data symbol subblock may be coded and modulated based on the SNR expected for the subblock. Each data symbol subblock may be transmitted as one element of the data symbol vector s, and the $N_T$ data symbol subblocks may be transmitted in parallel. An outage may then occur if any one of the $N_T$ data symbol subblocks cannot be decoded error free by the receiving entity.

If partial-CSI transmission without spatial spreading is used for the $N_T$ data symbol subblocks, then each subblock is transmitted from a respective transmit antenna. Each data symbol subblock would then observe the SNR achieved for the spatial channel corresponding to its transmit antenna. The receiving entity can estimate the SNR of each spatial channel, select an appropriate rate for each spatial channel based on its SNR, and provide the rates for all $N_T$ spatial channels to the transmitting entity. The transmitting entity can then encode and modulate the $N_T$ data symbol subblocks based on their selected rates.

The MIMO channel may change between time n when the rates are selected to time n+τ when the rates are actually used. This may be the case, for example, if the receiving entity has moved to a new location, if the MIMO channel changes faster than the feedback rate, and so on. The new channel response matrix $H_1$ at time n+τ may have the same capacity as the prior channel response matrix $H_0$ at time n, which may be expressed as:

$$Cap(H_0) = \sum_{i=1}^{N_T} \log_2(1+\gamma_i(n)) \qquad \text{Eq (27)}$$
$$= \sum_{i=1}^{N_T} \log_2(1+\gamma_i(n+\tau)) = Cap(H_1),$$

where $\gamma_i(n)$ is the SNR of spatial channel i at time n and $\log_2(1+\gamma_i(n))$ is the capacity of spatial channel i at time n. Even if the capacities of $H_0$ and $H_1$ are the same, the capacities of the individual spatial channels may have changed between time n and time n+τ, so that $\gamma_i(n)$ may not be equal to $\gamma_i(n+\tau)$.

Without spatial spreading, the outage probability increases if $\gamma_i(n)<\gamma_i(n+\tau)$ for any spatial channel i. This is because a data symbol subblock sent on a spatial channel with a lower SNR is less likely to be decoded error free, and any data symbol subblock decoded in error corrupts the entire data symbol block under the above assumption.

If partial-CSI transmission with spatial spreading is used for the $N_T$ data symbol subblocks, then each subblock is spatially spread and transmitted from all $N_T$ transmit antennas. Each data symbol subblock would then be transmitted on a transmission channel formed by a combination of $N_T$ spatial channels of the MIMO channel and would observe an effective SNR that is a combination of the SNRs for these spatial channels. The transmission channel for each data symbol subblock is determined by the steering matrices used for spatial spreading. If a sufficient number of steering matrices is used to spatially spread the $N_T$ data symbol subblocks, then the effective SNR observed by each data symbol subblock will be approximately equal to the average SNR for all of the spatial channels when a powerful error correction code is employed. With spatial spreading, the outage probability may then be dependent on the average SNR of the spatial channels instead of the SNRs of the individual spatial channels. Thus, if the average SNR at time n+τ is approximately equal to the average SNR at time n, then the outage probability may be approximately the same even though the SNRs of the individual spatial channels may have changed between times n and n+τ.

Spatial spreading can thus improve performance for the case in which inaccurate partial CSI is available at the transmitting entity and/or receiving entity. The inaccurate partial CSI may result from mobility, inadequate feedback rate, and so on.

2. Multi-Carrier MIMO System

Spatial spreading may also be used for a multi-carrier MIMO system. Multiple carriers may be provided by orthogonal frequency division multiplexing (OFDM) or some other constructs. OFDM effectively partitions the overall system bandwidth into multiple ($N_F$) orthogonal frequency subbands, which are also referred to as tones, subcarriers, bins, and frequency channels. With OFDM, each subband is associated with a respective subcarrier that may be modulated with data. For an OFDM-based system, spatial spreading may be performed on each of the subbands used for data transmission.

For a MIMO system that utilizes OFDM (i.e., a MIMO-OFDM system), one data symbol vector s(k,n) may be formed for each subband k in each OFDM symbol period n. Vector s(k,n) contains up to $N_S$ data symbols to be sent via the $N_S$ eigenmodes or spatial channels of subband k in OFDM symbol period n. Up to $N_F$ vectors, s(k,n) for k=1 . . . $N_F$, may be transmitted concurrently on the $N_F$ subbands in one OFDM symbol period. For the MIMO-OFDM system, a transmission span can cover both time and frequency dimensions. The index m for transmission span may thus be substituted with k,n for subband k and OFDM symbol period n. A transmission span may cover one subband in one OFDM symbol period or multiple OFDM symbol periods and/or multiple subbands.

For the full-CSI transmission scheme, the channel response matrix H(k) for each subband k may be decomposed to obtain the $N_S$ eigenmodes of that subband. The eigenvalues in each diagonal matrix Λ(k), for k=1 . . . $N_F$, may be ordered such that the first column contains the largest eigenvalue, the second column contains the next largest eigenvalue, and so on, or $\lambda_1(k) \geq \lambda_2(k) \geq \ldots \geq \lambda_{N_S}(k)$, where $\lambda_l(k)$ is the eigenvalue in the l-th column of Λ(k) after the ordering. When the eigenvalues for each matrix H(k) are ordered, the eigenvectors (or columns) of the associated matrix E(k) for that subband are also ordered correspondingly. A "wideband" eigenmode may be defined as the set of same-order eigenmodes of all $N_F$ subbands after the ordering (e.g., the l-th wideband eigenmode includes the l-th eigenmode of all subbands). Each wideband eigenmode is associated with a respective set of $N_F$ eigenvectors for the $N_F$ subbands. The principle wideband eigenmode is the one associated with the largest eigenvalue in each matrix Λ(k) after the ordering. Data may be transmitted on the $N_S$ wideband eigenmodes.

For the partial-CSI transmission scheme, the transmitting entity may perform spatial spreading and spatial processing for each subband, and the receiving entity may perform receiver spatial processing and spatial despreading for each subband.

Each data symbol block may be transmitted in various manners in the MIMO-OFDM system. For example, each data symbol block may be transmitted as one entry of the vector s(k,n) for each of the NF subbands. In this case, each data symbol block is sent on all $N_F$ subbands and achieves frequency diversity in combination with spatial diversity provided by spatial spreading. Each data symbol block may also span one or multiple OFDM symbol periods. Each data symbol block may thus span frequency and/or time dimensions (by system design) plus spatial dimension (with spatial spreading).

The steering matrices may also be selected in various manners for the MIMO-OFDM system. The steering matrices for the subbands may be selected in a deterministic, pseudo-random, or permutated manner, as described above. For example, the L steering matrices in the set may be cycled through and selected in sequential order for subbands 1 through $N_F$ in OFDM symbol period n, then subbands 1 through $N_F$ in OFDM symbol period n+1, and so on. The number of steering matrices in the set may be less than, equal to, or greater than the number of subbands. The three cases described above for L=$N_M$, L<$N_M$, and L>$N_M$ may also be applied for the subbands, with $N_M$ being replaced with $N_F$.

3. MIMO System

Figure 5:
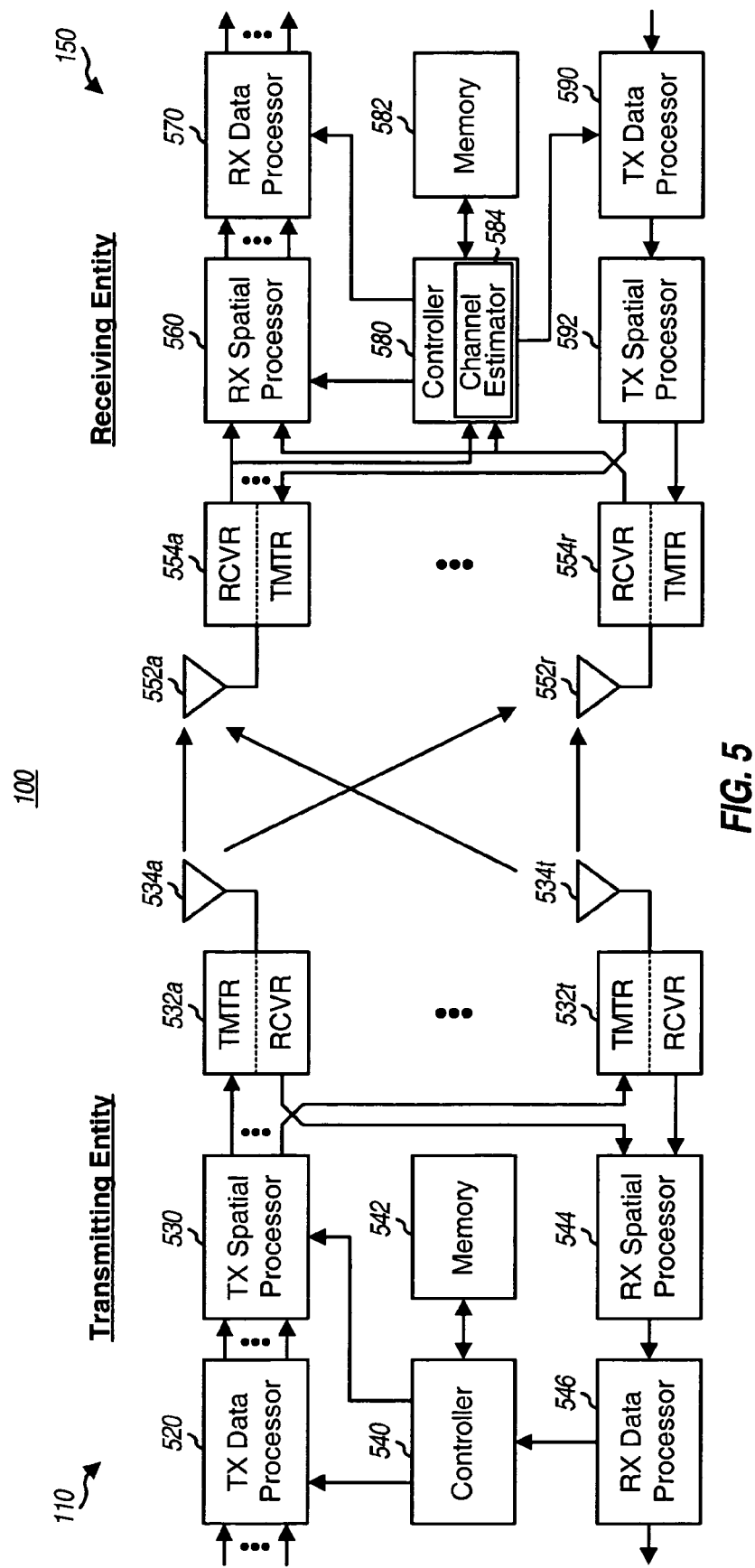
FIG. 5 shows a block diagram of the transmitting and receiving entities.

FIG. 5 shows a block diagram of transmitting entity 110 and receiving entity 150. At transmitting entity 110, a TX data processor 520 receives and processes (e.g., encodes, interleaves, and modulates) data and provides data symbols. A TX spatial processor 530 receives the data symbols, performs spatial spreading and spatial processing for full-CSI or partial-CSI transmission, multiplexes in pilot symbols, and provides $N_T$ transmit symbol streams to $N_T$ transmitter units (TMTR) 532a through 532t. Each transmitter unit 532 performs OFDM modulation (if applicable) and further conditions (e.g., converts to analog, filters, amplifies, and frequency upconverts) a respective transmit symbol stream to generate a modulated signal. $N_T$ transmitter units 532a through 532t provide $N_T$ modulated signals for transmission from $N_T$ antennas 534a through 534t, respectively.

At receiving entity 150, $N_R$ antennas 552a through 552r receive the $N_T$ transmitted signals, and each antenna 552 provides a received signal to a respective receiver unit (RCVR) 554. Each receiver unit 554 performs processing complementary to that performed by transmitter unit 532 (including OFDM demodulation, if applicable) and provides (1) received data symbols to an RX spatial processor 560 and (2) received pilot symbols to a channel estimator 584 within a controller 580. RX spatial processor 560 performs receiver spatial processing and spatial despreading on $N_R$ received symbol streams from $N_R$ receiver units 554 with spatial filter matrices and steering matrices, respectively, from controller 580 and provides $N_S$ recovered symbol streams. An RX data processor 570 then processes (e.g., demaps, deinterleaves, and decodes) the recovered symbols and provides decoded data.

Channel estimator 584 may derive Ĥ(m), which is an estimate of the channel response matrix H(m), based on pilot symbols transmitted without spatial spreading. Alternatively, channel estimator 584 may directly derive $\hat{H}_{eff}(m)$, which is an estimate of the effective channel response matrix $\hat{H}_{eff}(m)$, based on pilot symbols transmitted with spatial spreading. In any case, $\hat{H}(m)$ or $\hat{H}_{eff}(m)$ may be used to derive the spatial filter matrix. Channel estimator 584 further estimates the SNR of each transmission channel based on received pilot symbols and/or received data symbols. The MIMO channel includes $N_S$ transmission channels for each subband, but these transmission channels can be different depending on (1) whether full-CSI or partial-CSI transmission is used, (2) whether or not spatial spreading was performed, and (3) the specific spatial processing technique used by the receiving entity. Controller 580 selects a suitable rate for each transmission channel based on its SNR. Each selected rate is associated with a particular coding scheme and a particular modulation scheme, which collectively determine a data rate. The same or different rates may be selected for the $N_S$ transmission channels.

The rates for all transmission channels, other information, and traffic data are processed (e.g., encoded and modulated) by a TX data processor 590, spatially processed (if needed) by a TX spatial processor 592, conditioned by transmitter units 554a through 554r, and sent via antennas 552a through 552r. At transmitting entity 110, the $N_R$ signals sent by receiving entity 150 are received by antennas 534a through 534t, conditioned by receiver units 532a through 532t, spatially processed by an RX spatial processor 544, and further processed (e.g., demodulated and decoded) by an RX data processor 546 to recover the selected rates. Controller 540 may then direct TX data processor 520 to process data for each transmission channel based on the rate selected for that transmission channel.

Controllers 540 and 580 also control the operation of various processing units at transmitting entity 110 and receiving entity 150, respectively. Memory units 542 and 582 store data and/or program code used by controllers 540 and 580, respectively.

Figure 6:
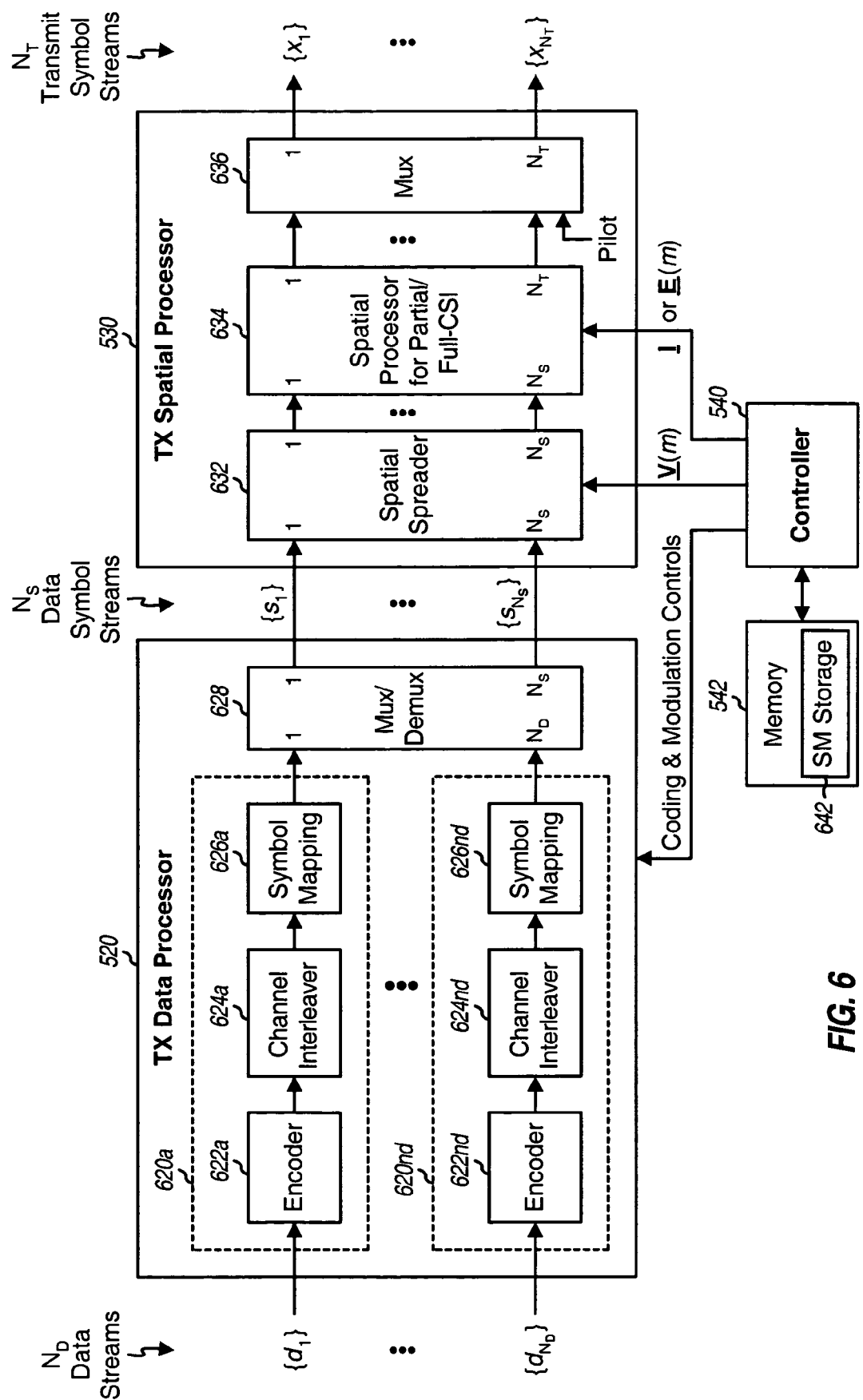
FIG. 6 shows a transmit (TX) data processor and a TX spatial processor at the transmitting entity.

FIG. 6 shows a block diagram of an embodiment of TX data processor 520 and TX spatial processor 530 at transmitting entity 110. For this embodiment, TX data processor 520 includes $N_D$ TX data stream processors 620a through 620nd for $N_D$ data streams $\{d_l\}$, for $l=1 \ldots N_D$, where in general $N_D \geq 1$.

Within each TX data stream processor 620, an encoder 622 receives and encodes its data stream $\{d_l\}$ based on a coding scheme and provides code bits. Each data packet in the data stream is encoded separately to obtain a corresponding code block or coded data packet. The coding increases the reliability of the data transmission. The coding scheme may include cyclic redundancy check (CRC) generation, convolutional coding, Turbo coding, low density parity check (LDPC) coding, block coding, other coding, or a combination thereof. With spatial spreading, the SNR can vary across a code block even if the MIMO channel is static over the code block. A sufficiently powerful coding scheme may be used to combat the SNR variation across the code block, so that coded performance is proportional to the average SNR across the code block. Some exemplary coding schemes that can provide good performance for spatial spreading include Turbo code (e.g., the one defined by IS-856), LDPC code, and convolutional code.

A channel interleaver 624 interleaves (i.e., reorders) the code bits based on an interleaving scheme to achieve frequency, time and/or spatial diversity. The interleaving may be performed across a code block, a partial code block, multiple code blocks, and so on. A symbol mapping unit 626 maps the interleaved bits based on a modulation scheme and provides a stream of data symbols $\{s_l\}$. Unit 626 groups each set of B interleaved bits to form a B-bit value, where $B \geq 1$, and further maps each B-bit value to a specific modulation symbol based on the modulation scheme (e.g., QPSK, M-PSK, or M-QAM, where $M=2^B$). Unit 626 provides a block of data symbols for each code block.

In FIG. 6, $N_D$ TX data stream processors 620 process $N_D$ data streams. One TX data stream processor 620 may also process the ND data streams, e.g., in a time division multiplex (TDM) manner.

Data may be transmitted in various manners in the MIMO system. For example, if $N_D=1$, then one data stream is processed, demultiplexed, and transmitted on all $N_S$ transmission channels of the MIMO channel. If $N_D=N_S$, then one data stream may be processed and transmitted on each transmission channel. In any case, the data to be sent on each transmission channel may be encoded and modulated based on the rate selected for that transmission channel. A multiplexer/demultiplexer (Mux/Demux) 628 receives and multiplexes/demultiplexes the data symbols for the $N_D$ data streams into $N_S$ data symbol streams, one data symbol stream for each transmission channel. If $N_D=1$, then Mux/Demux 628 demultiplexes the data symbols for one data stream into $N_S$ data symbol streams. If $N_D=N_S$, then Mux/Demux 628 can simply provide the data symbols for each data stream as a respective data symbol stream.

TX spatial processor 530 receives and spatially processes the $N_S$ data symbol streams. Within TX spatial processor 530, a spatial spreader 632 receives the $N_S$ data symbol streams, performs spatial spreading for each transmission span m with the steering matrix V(m) selected for that transmission span, and provides $N_S$ spread symbol streams. The steering matrices may be retrieved from a steering matrix (SM) storage 642 within memory unit 542 or generated by controller 540 as they are needed. A spatial processor 634 then spatially processes the $N_S$ spread symbol streams with the identity matrix I for partial-CSI transmission or with the matrices E(m) of eigenvectors for full-CSI transmission. A multiplexer 636 multiplexes the transmit symbols from spatial processor 634 with pilot symbols (e.g., in a time division multiplexed manner) and provides $N_T$ transmit symbol streams for the $N_T$ transmit antennas.

Figure 7:
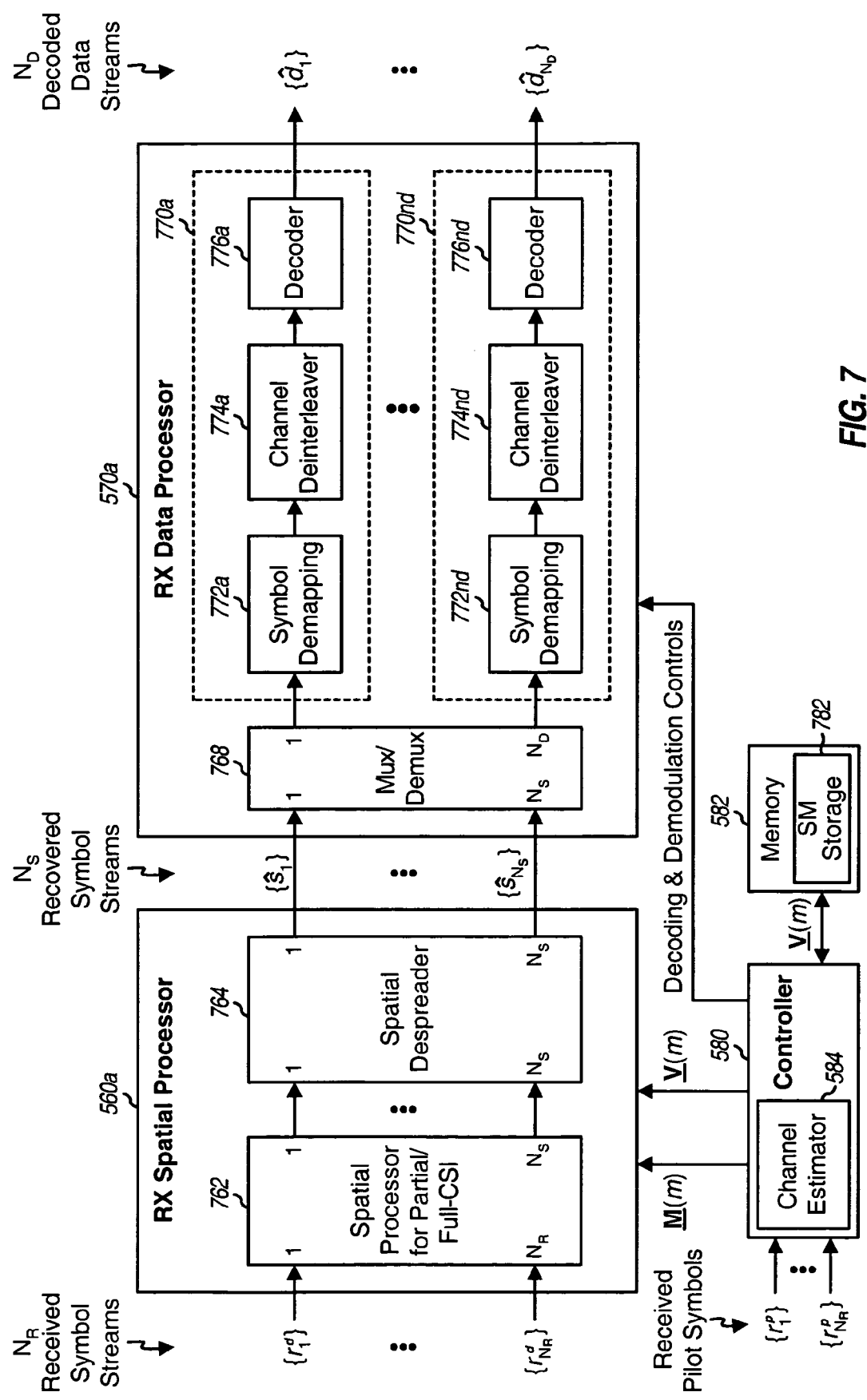
FIG. 7 shows a receive (RX) spatial processor and an RX data processor at the receiving entity.

FIG. 7 shows a block diagram of an RX spatial processor 560a and an RX data processor 570a, which are one embodiment of RX spatial processor 560 and RX data processor 570, respectively, at receiving entity 150. $N_R$ receiver units 554a through 554r provide received pilot symbols, $\{r_i^p\}$ for $i=1 \ldots N_R$, to channel estimator 584. Channel estimator 584 estimates the channel response matrix H(m) based on the received pilot symbols and further estimates the SNR of each transmission channel. Controller 580 derives a spatial filter matrix M(m) and possibly a diagonal matrix D(m) for each transmission span m based on the channel response matrix H(m) and possibly the steering matrix V(m). Receiving entity 150 is synchronized with transmitting entity 110 so that both entities use the same steering matrix V(m) for each transmission span m. The matrix M(m) may be derived as shown in equation (10) for the full-CSI transmission and as shown in equations (17) and (23) for the partial-CSI transmission with the CCMI and MMSE techniques, respectively. The matrix M(m) may or may not include the steering matrix V(m) depending on whether the receiver spatial processing and spatial despreading are performed jointly or separately.

FIG. 7 shows receiver spatial spreading and spatial despreading being performed separately. RX spatial processor 560 obtains received data symbols, $\{r_i^d\}$ for $i=1 \ldots N_R$, from receiver units 554a through 554r and the matrices M(m) and V(m) from controller 580. Within RX spatial processor 560, a spatial processor 762 performs receiver spatial processing on the received data symbols for each transmission span with the matrices M(m). A spatial despreader 764 then performs spatial despreading with the matrix V(m) and provides recovered symbols to RX data processor 570. The receiver spatial processing and spatial despreading may also be performed jointly using the effective MIMO channel estimate, as described above.

For the embodiment shown in FIG. 7, RX data processor 570a includes a multiplexer/demultiplexer (Mux/Demux) 768 and $N_D$ RX data stream processors 770a through 770nd for the $N_D$ data streams. Mux/Demux 768 receives and multiplexes/demultiplexes the $N_S$ recovered symbol streams for the $N_S$ transmission channels into $N_D$ recovered symbol streams for the $N_D$ data streams. Within each RX data stream processor 770, a symbol demapping unit 772 demodulates the recovered symbols for its data stream in accordance with the modulation scheme used for that stream and provides demodulated data. A channel deinterleaver 774 deinterleaves the demodulated data in a manner complementary to the interleaving performed on that stream by transmitting entity 110. A decoder 776 decodes the deinterleaved data in a manner complementary to the encoding performed by transmitting entity 110 on that stream. For example, a Turbo decoder or a Viterbi decoder may be used for decoder 776 if Turbo or convolutional coding, respectively, is performed by transmitting entity 110. Decoder 776 provides a decoded data stream, which includes a decoded data packet for each data symbol block.

Figure 8:
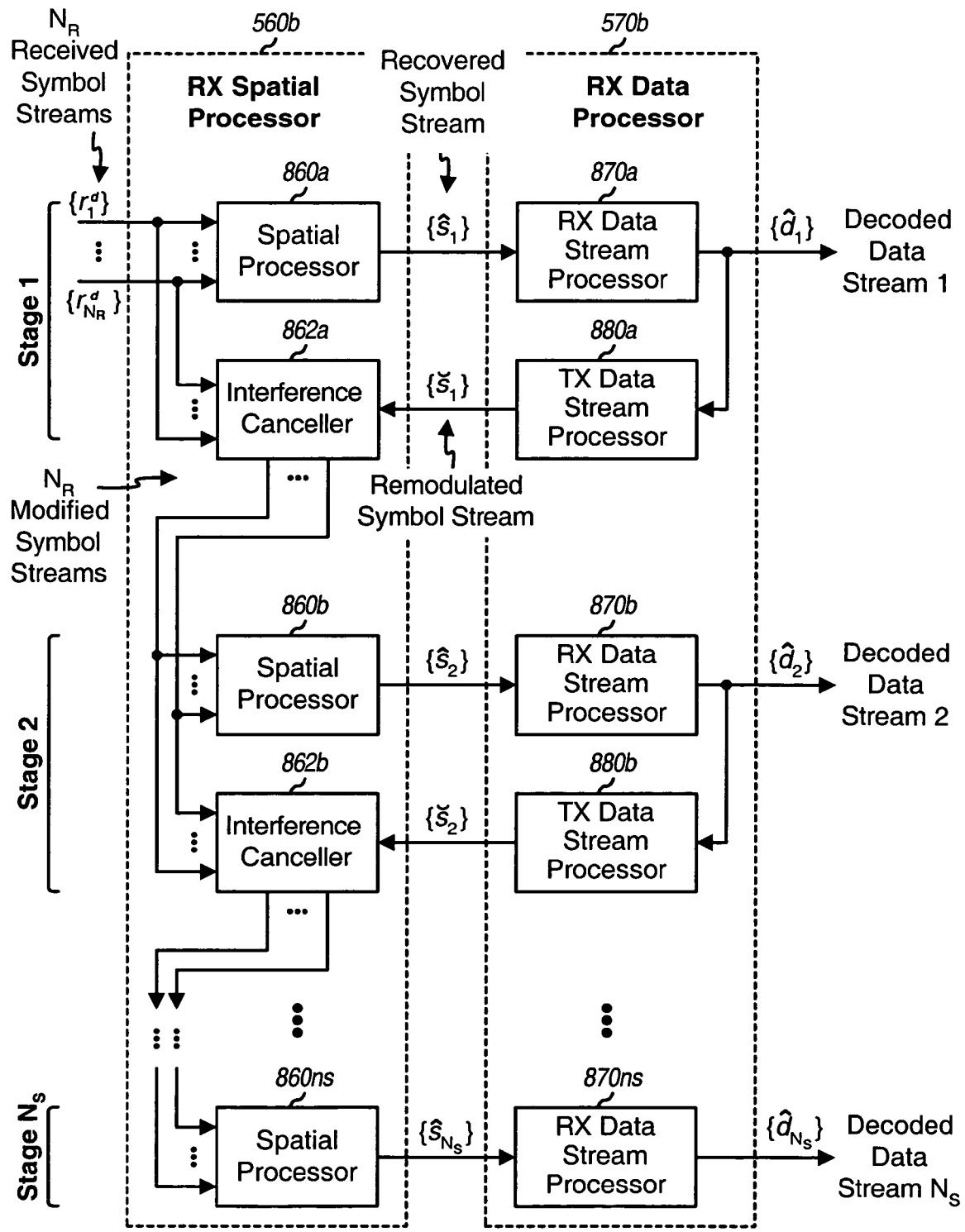
FIG. 8 shows an RX spatial processor and an RX data processor that implement a successive interference cancellation (SIC) technique.

FIG. 8 shows a block diagram of an RX spatial processor 560b and an RX data processor 570b, which implement the SIC technique for receiving entity 150. For simplicity, $N_D=N_S$ and RX spatial processor 560b and RX data processor 570b implement $N_S$ cascaded receiver processing stages for the $N_S$ data symbol streams. Each of stages 1 to $N_S-1$ includes a spatial processor 860, an interference canceller 862, an RX data stream processor 870, and a TX data stream processor 880. The last stage includes only a spatial processor 860ns and an RX data stream processor 870ns. Each RX data stream processor 870 includes a symbol demapping unit, a channel deinterleaver, and a decoder, as shown in FIG. 7. Each TX data stream processor 880 includes an encoder, a channel interleaver, and a symbol mapping unit, as shown in FIG. 6.

For stage 1, spatial processor 860a performs receiver spatial processing on the $N_R$ received symbol streams and provides one recovered symbol stream $\{\hat{s}_1\}$. RX data stream processor 870a demodulates, deinterleaves, and decodes the recovered symbol stream $\{\hat{s}_1\}$ and provides a corresponding decoded data stream $\{\hat{d}_1\}$. TX data stream processor 880a encodes, interleaves, and modulates the decoded data stream $\{\hat{d}_1\}$ in the same manner performed by transmitting entity 110 for that stream and provides a remodulated symbol stream $\{\check{s}_1\}$. Interference canceller 862a spatially spreads the remodulated symbol stream $\{\check{s}_1\}$ with the steering matrix V(m) and further multiplies the results with the channel response matrix $\hat{H}(m)$ to obtain $N_R$ interference components due to data symbol stream $\{s_1\}$. The $N_R$ interference components are subtracted from the $N_R$ received symbol streams to obtain $N_R$ modified symbol streams, which are provided to stage 2.

Each of stages 2 through $N_S-1$ performs the same processing as stage 1, albeit on the $N_R$ modified symbol streams from the preceding stage instead of the $N_R$ received symbol streams. The last stage performs spatial processing and decoding on the $N_R$ modified symbol streams from stage $N_S-1$ and does not perform interference estimation and cancellation.

Spatial processors 860a through 860ns may each implement the CCMI, MMSE, or some other technique. Each spatial processor 860 multiplies an input (received or modified) symbol vector $r_{sic}^l(m)$ with a spatial filter matrix $M_{sic}^l(m)$ and the steering matrix V(m) to obtain a recovered symbol vector $\hat{s}_{sic}^l(m)$ and provides the recovered symbol stream for that stage. The matrix $M_{sic}^l(m)$ is derived based on a reduced channel response matrix $\hat{H}^l(m)$ for the stage. The matrix $\hat{H}^l(m)$ is equal to $\hat{H}(m)$ with the columns for all of the data symbol streams already recovered in prior stages removed.

4. Rate Selection and Control

For both full-CSI and partial-CSI transmission, the receiving entity can estimate the SNR of each transmission channel. The SNR computation is dependent on (1) whether full-CSI or partial-CSI transmission is used, (2) whether spatial spreading is performed, and (3) the particular receiver spatial processing technique (e.g., CCMI, MMSE, or SIC) used by the receiving entity in the case of partial-CSI transmission. For a MIMO-OFDM system, the SNR for each subband of each transmission channel may be estimated and averaged to obtain the SNR of the transmission channel. In any case, an operating SNR, $\gamma_{op}(l)$, for each transmission channel may be computed based on the SNR of the transmission channel, $\gamma_{pd}(l)$, and an SNR offset, $\gamma_{os}(l)$, as follows:

$$\gamma_{op}(l)=\gamma_{pd}(l)+\gamma_{os}(l), \qquad \text{Eq (28)}$$

where the units are in decibels (dB). The SNR offset may be used to account for estimation error, variability in the channel, and other factors. A suitable rate is selected for each transmission channel based on the operating SNR of the transmission channel.

The MIMO system may support a specific set of rates. One of the supported rates may be for a null rate, which is a data rate of zero. Each of the remaining rates is associated with a particular non-zero data rate, a particular coding scheme or code rate, a particular modulation scheme, and a particular minimum SNR required to achieve a desired level of performance, e.g., 1% packet error rate (PER) for a non-fading AWGN channel. For each supported non-zero rate, the required SNR may be obtained based on the specific system design (such as the particular code rate, interleaving scheme, and modulation scheme used by the system for that rate) and for an AWGN channel. The required SNR may be obtained by computer simulation, empirical measurements, and so on, as is known in the art. The set of supported rates and their required SNRs may be stored in a look-up table.

The operating SNR, $\gamma_{op}(l)$, of each transmission channel may be provided to the look-up table, which then returns the rate q(l) for that transmission channel. This rate is the highest supported rate with a required SNR, $\gamma_{req}(l)$, that is less than or equal to the operating SNR, or $\gamma_{req}(l) \leq \gamma_{op}(l)$. The receiving entity can thus select the highest possible rate for each transmission channel based on its operating SNR.

5. Steering Matrix Generation

The steering matrices used for spatial spreading may be generated in various manners, and some exemplary schemes are described below. A set of L steering matrices may be pre-computed and stored at the transmitting and receiving entities and thereafter retrieved for use as they are needed. Alternatively, these steering matrices may be computed in real time as they are needed.

The steering matrices should be unitary matrices and satisfy the following condition:

$$V^H(i) \cdot V(i) = I, \text{ for } i=1 \ldots L. \qquad \text{Eq (29)}$$

Equation (28) indicates that each column of V(i) should have unit energy and the Hermitian inner product of any two columns of V(i) should be zero. This condition ensures that the $N_S$ data symbols sent simultaneously using the steering matrix V(i) have the same power and are orthogonal to one another prior to transmission.

Some of the steering matrices may also be uncorrelated so that the correlation between any two uncorrelated steering matrices is zero or a low value. This condition may be expressed as:

$$C(ij) = V^H(i) \cdot V(j) \approx 0, \text{ for } i=1 \ldots L, j=1 \ldots L, \text{ and } i \ne j, \qquad \text{Eq (30)}$$

where C(ij) is the correlation matrix for V(i) and V(j) and 0 is a matrix of all zeros. The condition in equation (30) may improve performance for some applications but is not necessary for most applications.

The set of L steering matrices {V} may be generated using various schemes. In a first scheme, the L steering matrices are generated based on matrices of random variables. An $N_S \times N_T$ matrix G with elements that are independent identically distributed complex Gaussian random variables, each having zero mean and unit variance, is initially generated. An $N_T \times N_T$ correlation matrix of G is computed and decomposed using eigenvalue decomposition as follows:

$$R_G = G^H \cdot G = E_G \cdot D_G \cdot E_G^H. \qquad \text{Eq (31)}$$

The matrix $E_G$ is used as a steering matrix V(i) and added to the set. The process is repeated until all L steering matrices are generated.

In a second scheme, the L steering matrices are generated based on a set of $(\log_2 L)+1$ independent isotropically distributed (IID) unitary matrices, as follows:

$$V(l_1 l_2 \ldots l_Q) = \Omega_1^{l_1} \cdot \Omega_2^{l_2} \ldots \cdot \Omega_Q^{l_Q} \cdot V_0, \text{ for } l_1, l_2, \ldots, l_Q \in \{0,1\}, \qquad \text{Eq (32)}$$

where $V_0$ is an $N_T \times N_S$ independent isotropically distributed unitary matrix;

$i = l_1 l_2 \ldots l_Q$, where $Q = \log_2 L$ and $l_j$ is the j-th bit of index i; and $\Omega_j^{l_j}$, for j=1 ... Q, is an $N_T \times N_T$ IID unitary matrix.

The second scheme is described by T. L. Marzetta et al. in "Structured Unitary Space-Time Autocoding Constellations," IEEE Transaction on Information Theory, Vol. 48, No. 4, Apr. 2002.

In a third scheme, the L steering matrices are generated by successively rotating an initial unitary steering matrix V(1) in an $N_T$-dimensional complex space, as follows:

$$V(i+1) = \Theta^i \cdot V(1), \text{ for } i=1 \ldots L-1, \qquad \text{Eq (33)}$$

where $\Theta^i$ is an $N_T \times N_T$ diagonal unitary matrix with elements that are L-th roots of unity. The third scheme is described by B. M. Hochwald et al. in "Systematic Design of Unitary Space-Time Constellations," IEEE Transaction on Information Theory, Vol. 46, No. 6, Sep. 2000.

In a fourth scheme, the set of L steering matrices is generated with a base matrix B and different scalars. The base matrix may be a Walsh matrix, a Fourier matrix, or some other matrix. A 2×2 Walsh matrix may be expressed as $$\underline{W}_{2 \times 2} = \begin{bmatrix} 1 & 1 \\ 1 & -1 \end{bmatrix}.$$

A larger size Walsh matrix $W_{2N \times 2N}$ may be formed from a smaller size Walsh matrix $W_{N \times N}$, as follows:

$$\underline{W}_{2N \times 2N} = \begin{bmatrix} \underline{W}_{N \times N} & \underline{W}_{N \times N} \\ \underline{W}_{N \times N} & -\underline{W}_{N \times N} \end{bmatrix} \qquad \text{Eq (34)}$$

Walsh matrices have dimensions that are powers of two.

An $N_T \times N_T$ Fourier matrix D has element $w_{n,m}$ in the n-th row of the m-th column, which may be expressed as:

$$w_{n,m} = e^{-j2\pi \frac{(n-1)(m-1)}{N_T}}, \qquad \text{Eq (35)}$$

for $n = \{1 \ldots N_T\}$ and $m = \{1 \ldots N_T\}$, where n is a row index and m is a column index. Fourier matrices of any square dimension (e.g., 2, 3, 4, 5, and so on) may be formed.

An $N_T \times N_T$ Walsh matrix W, Fourier matrix D, or some other matrix may be used as the base matrix B to form other steering matrices. Each of rows 2 through $N_T$ of the base matrix may be independently multiplied with one of M different possible scalars, where M>1. $M^{N_T-1}$ different steering matrices may be obtained from $M^{N_T-1}$ different permutations of the M scalars for the $N_T-1$ rows. For example, each of rows 2 through $N_T$ may be independently multiplied with a scalar of +1, −1, +j, or −j, where $j=\sqrt{-1}$. For $N_T=4$ and M=4, 64 different steering matrices may be generated from the base matrix B with the four different scalars. Additional steering matrices may be generated with other scalars, e.g., $e^{\pm j3\pi/4}$, $e^{\pm j\pi/4}$, $e^{\pm j\pi/8}$, and so on. In general, each row of the base matrix may be multiplied with any scalar having the form $e^{j\theta}$, where $\theta$ may be any phase value. $N_T \times N_T$ steering matrices may be generated as $V(i) = g_{N_T} \cdot B(i)$, where $g_{N_T} = 1/\sqrt{N_T}$ and B(i) is the i-th matrix generated with the base matrix B. The scaling by $g_{N_T}$ ensures that each column of V(i) has unit power.

Other schemes may also be used to generate the set of L steering matrices, and this is within the scope of the invention. In general, the steering matrices may be generated in a pseudo-random manner (e.g., such as the first scheme) or a deterministic manner (e.g., such as the second, third, and fourth schemes).

The spatial spreading techniques described herein may be implemented by various means. For example, these techniques may be implemented in hardware, software, or a combination thereof. For a hardware implementation, the processing units for spatial spreading at the transmitting entity and spatial despreading at the receiving entity may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof.

For a software implementation, the spatial spreading techniques may be implemented with modules (e.g., procedures, functions, and so on) that perform the functions described herein. The software codes may be stored in memory units (e.g., memory units 542 and 582 in FIG. 5) and executed by a processor (e.g., controllers 540 and 580 in FIG. 5). The memory unit may be implemented within the processor or external to the processor, in which case it can be communicatively coupled to the processor via various means as is known in the art.

Headings are included herein for reference and to aid in locating certain sections. These headings are not intended to limit the scope of the concepts described therein under, and these concepts may have applicability in other sections throughout the entire specification.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A method of transmitting data from a transmitting entity to a receiving entity in a wireless multiple-input multiple-output (MIMO) communication system, comprising:
   processing data to obtain a plurality of streams of data symbols for transmission on a plurality of transmission channels in a MIMO channel between the transmitting entity and the receiving entity;
   performing spatial spreading on the plurality of streams of data symbols with at least two different steering matrices for a plurality of subbands to obtain a plurality of streams of spread symbols, wherein the spatial spreading with the plurality of steering matrices randomizes the plurality of transmission channels for the plurality of streams of data symbols;
   performing spatial processing on the plurality of streams of spread symbols to obtain a plurality of streams of transmit symbols for transmission from a plurality of transmit antennas at the transmitting entity; and transmitting the plurality of streams of transmit symbols from the plurality of transmit antennas.

2. The method of claim 1, wherein the performing spatial processing comprises
   multiplying the plurality of streams of spread symbols with matrices of eigenvectors to transmit the plurality of streams of spread symbols on a plurality of eigenmodes of the MIMO channel.

3. The method of claim 1, wherein the performing spatial processing comprises
   providing each of the plurality of streams of spread symbols as one of the plurality of streams of transmit symbols.

4. The method of claim 1, wherein the processing data comprises
   encoding and modulating data for each of the plurality of streams of data symbols based on a rate selected for the stream of data symbols.

5. The method of claim 4, further comprising:
   obtaining the rate for each stream of data symbols, the rate being selected based on a signal-to-noise-and-interference ratio (SNR) of a transmission channel for the stream of data symbols.

6. The method of claim 1, wherein the processing data comprises
   encoding and modulating each of a plurality of packets of data to obtain a block of data symbols, and
   multiplexing a plurality of blocks of data symbols generated for the plurality of packets of data onto the plurality of streams of data symbols.

7. The method of claim 6, wherein the encoding and modulating comprise
   encoding each packet of data based on a Turbo code, a convolutional code, or a low density parity check (LDPC) code to obtain a block of coded data, and
   symbol mapping each block of coded data based on a modulation scheme to obtain a block of data symbols.

8. The method of claim 6, wherein the multiplexing the plurality of blocks of data symbols comprises
   multiplexing each block of data symbols onto one of the plurality of streams of data symbols.

9. The method of claim 6, wherein the multiplexing the plurality of blocks of data symbols comprises
   multiplexing each block of data symbols onto all of the plurality of streams of data symbols.

10. The method of claim 1, wherein the performing spatial spreading comprises
    performing spatial processing on the plurality of streams of data symbols using a set of L steering matrices, where L is an integer greater than one.

11. The method of claim 10, further comprising:
    generating the L steering matrices as unitary matrices having orthogonal columns.

12. The method of claim 10, further comprising:
    selecting a steering matrix from among the L steering matrices for each time interval, and wherein the spatial spreading is performed for each time interval with the steering matrix selected for the time interval.

13. The method of claim 10, further comprising:
    selecting a steering matrix from among the L steering matrices for each group of at least one frequency subband, and wherein the spatial spreading is performed for each group of at least one frequency subband with the steering matrix selected for the group.

14. The method of claim 1, further comprising:
    processing each of the plurality of streams of transmit symbols for orthogonal frequency division multiplexing (OFDM).

15. An apparatus in a wireless multiple-input multiple-output (MIMO) communication system, comprising:
    a data processor to process data to obtain a plurality of streams of data symbols for transmission on a plurality of transmission channels in a MIMO channel between a transmitting entity and a receiving entity in the MIMO system;
    a spatial spreader to perform spatial spreading on the plurality of streams of data symbols with at least two different steering matrices for a plurality of subbands to obtain a plurality of streams of spread symbols, wherein the spatial spreading with the plurality of steering matrices randomizes the plurality of transmission channels for the plurality of streams of data symbols;
    a spatial processor to perform spatial processing on the plurality of streams of spread symbols to obtain a plurality of streams of transmit symbols for transmission from a plurality of transmit antennas at the transmitting entity and a transmitter configured to transmit the plurality of streams of transmit symbols from the plurality of transmit antennas.

16. The apparatus of claim 15, wherein the spatial processor multiplies the plurality of streams of spread symbols with matrices of eigenvectors to transmit the plurality of streams of spread symbols on a plurality of eigenmodes of the MIMO channel.

17. The apparatus of claim 15, wherein the spatial processor provides each of the plurality of streams of spread symbols as one of the plurality of streams of transmit symbols.

18. The apparatus of claim 15, wherein the data processor encodes and modulates data for each of the plurality of streams of data symbols in accordance with a rate selected based on a signal-to-noise-and-interference ratio (SNR) of a transmission channel used for the stream of data symbols.

19. The apparatus of claim 15, wherein the data processor encodes and modulates each of a plurality of packets of data to obtain a block of data symbols, and multiplexes a plurality of blocks of data symbols generated for the plurality of packets of data onto the plurality of streams of data symbols.

20. The apparatus of claim 15, further comprising:
a controller to select a steering matrix from among L steering matrices for each time interval, where L is an integer greater than one, and wherein the spatial spreader performs spatial spreading for each time interval with the steering matrix selected for the time interval.

21. The apparatus of claim 15, wherein the spatial spreading by the spatial spreader results in whitened interference and noise observed by the receiving entity for the plurality of streams of data symbols after spatial despreading by the receiving entity.

22. The apparatus of claim 15, wherein the MIMO channel includes plurality of spatial channels, and wherein the spatial spreading by the spatial spreader results in each of the plurality of transmission channels achieving a signal-to-noise-and-interference ratio (SNR) that is an average of SNRs of the plurality of spatial channels.

23. An apparatus in a wireless multiple-input multiple-output (MIMO) communication system, comprising:
means for processing data to obtain a plurality of streams of data symbols for transmission on a plurality of transmission channels in a MIMO channel between a transmitting entity and a receiving entity in the MIMO system;
means for performing spatial spreading on the plurality of streams of data symbols with at least two different steering matrices for a plurality of subbands to obtain a plurality of streams of spread symbols, wherein the spatial spreading with the plurality of steering matrices randomizes the plurality of transmission channels for the plurality of streams of data symbols;
means for performing spatial processing on the plurality of streams of spread symbols to obtain a plurality of streams of transmit symbols for transmission from a plurality of transmit antennas at the transmitting entity
means for transmitting the plurality of streams of transmit symbols from the plurality of transmit antennas.

24. The apparatus of claim 23, wherein the means for performing spatial processing comprises
means for multiplying the plurality of streams of spread symbols with matrices of eigenvectors to transmit the plurality of streams of spread symbols on a plurality of eigenmodes of the MIMO channel.

25. The apparatus of claim 23, wherein the means for performing spatial processing comprises
means for providing each of the plurality of streams of spread symbols as one of the plurality of streams of transmit symbols.

26. The apparatus of claim 23, wherein the means for processing data comprises
means for encoding and modulating data for each of the plurality of streams of data symbols in accordance with a rate selected based on a signal-to-noise-and-interference ratio (SNR) of a transmission channel for the stream of data symbols.

27. The apparatus of claim 23, wherein the means for processing data comprises
means for encoding and modulating each of a plurality of packets of data to obtain a block of data symbols, and
means for multiplexing a plurality of blocks of data symbols generated for the plurality of packets of data onto the plurality of streams of data symbols.

28. The apparatus of claim 23, further comprising:
means for selecting a steering matrix from among L steering matrices for each time interval, where L is an integer greater than one, and wherein the spatial spreading for each time interval is performed with the steering matrix selected for the time interval.

* * * * *